United States Patent
Amos et al.

(10) Patent No.: US 9,855,061 B2
(45) Date of Patent: Jan. 2, 2018

(54) EQUIPMENT FOR INSERTING A JOINT PROSTHESIS, IN PARTICULAR A KNEE PROSTHESIS

(75) Inventors: Balzarini Amos, Norderstedt (DE); Marco Iredi, Norderstedt (DE); Klaus Dmuschewsky, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 1109 days.

(21) Appl. No.: 14/113,092

(22) PCT Filed: Apr. 19, 2012

(86) PCT No.: PCT/EP2012/057163
§ 371 (c)(1),
(2), (4) Date: Oct. 21, 2013

(87) PCT Pub. No.: WO2012/143444
PCT Pub. Date: Oct. 26, 2012

(65) Prior Publication Data
US 2014/0046331 A1 Feb. 13, 2014

(30) Foreign Application Priority Data
Apr. 21, 2011 (EP) .................................. 11163566

(51) Int. Cl.
*A61B 17/17* (2006.01)
*A61B 17/16* (2006.01)
(Continued)

(52) U.S. Cl.
CPC ........ *A61B 17/1675* (2013.01); *A61B 17/155* (2013.01); *A61B 17/1764* (2013.01);
(Continued)

(58) Field of Classification Search
CPC ..... A61B 17/151; A61B 17/155; A61B 17/17; A61B 17/1717
See application file for complete search history.

(56) References Cited

U.S. PATENT DOCUMENTS 5,049,149 A * 9/1991 Schmidt ................. A61B 17/15
606/87
2008/0147071 A1 6/2008 Serra et al.

FOREIGN PATENT DOCUMENTS

FR 2732581 A1 * 10/1996 ............. A61B 17/15

OTHER PUBLICATIONS

International Search Report and Written Opinion dated May 22, 2012, directed to International Application No. PCT/EP2012/057163; 9 pages.

* cited by examiner

*Primary Examiner* — Anu Ramana
(74) *Attorney, Agent, or Firm* — Morrison & Foerster LLP

(57) ABSTRACT

Equipment for inserting a joint prosthesis, in particular a femur component of a knee prosthesis, comprises a base frame having a guiding plate and a laterally protruding primary gage, a fastening device on the bone, and a curved milling gage having a main body and a guiding piece, which can be moved along a curved guiding path relative to the main body and has a receptacle for an abrasive tool. Furthermore, the equipment comprises an aligning device, which places the curved milling gage in a clearly defined relative position when the curved milling gage is inserted into the base frame. Due to the precise positioning in conjunction with the curved guiding path, the mounting seat can be prepared easily without damaging surrounding tissue.

(Continued)

Thus, even large and complexly shaped prostheses, such as knee joint prosthesis, can be reproducibly inserted in an easy and safe manner.

52 Claims, 17 Drawing Sheets

(51) Int. Cl.
  *A61B 17/15* (2006.01)
  *A61B 90/00* (2016.01)
  *A61B 17/14* (2006.01)
(52) U.S. Cl.
  CPC ........... *A61B 17/144* (2016.11); *A61B 17/154* (2013.01); *A61B 17/164* (2013.01); *A61B 17/1615* (2013.01); *A61B 17/1642* (2013.01); *A61B 17/1659* (2013.01); *A61B 17/1735* (2013.01); *A61B 2017/1602* (2013.01); *A61B 2090/034* (2016.02)

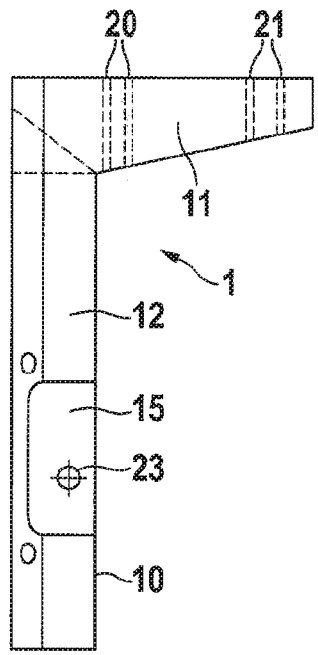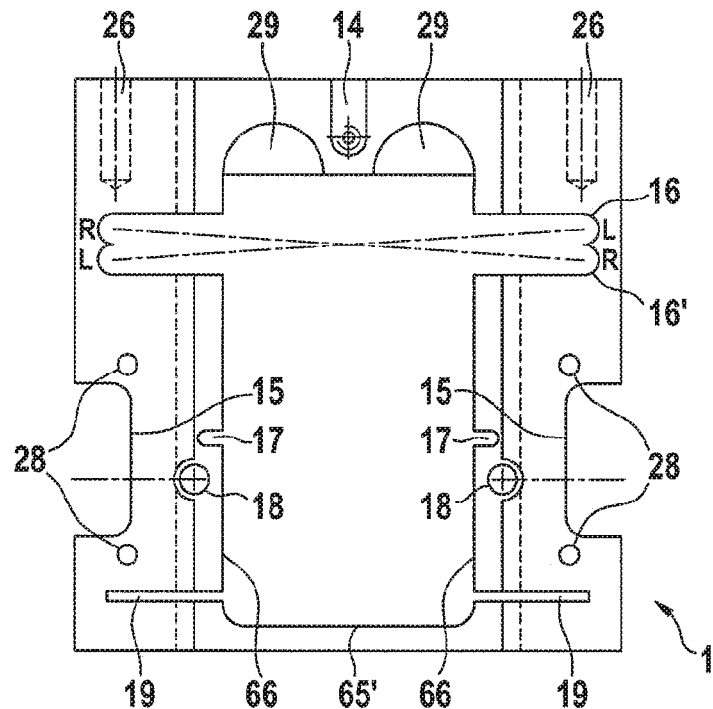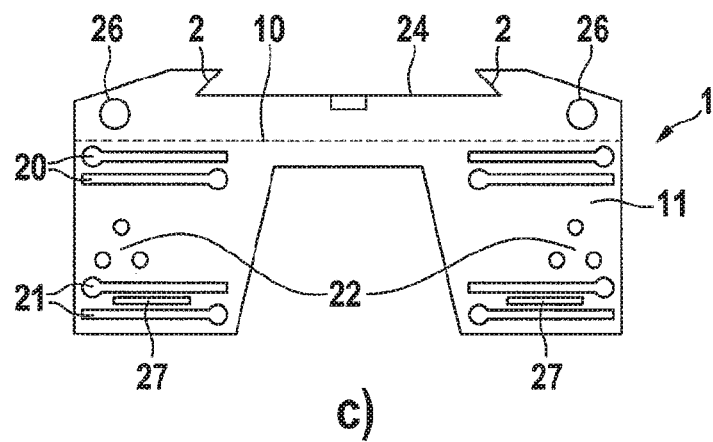
Fig. 1

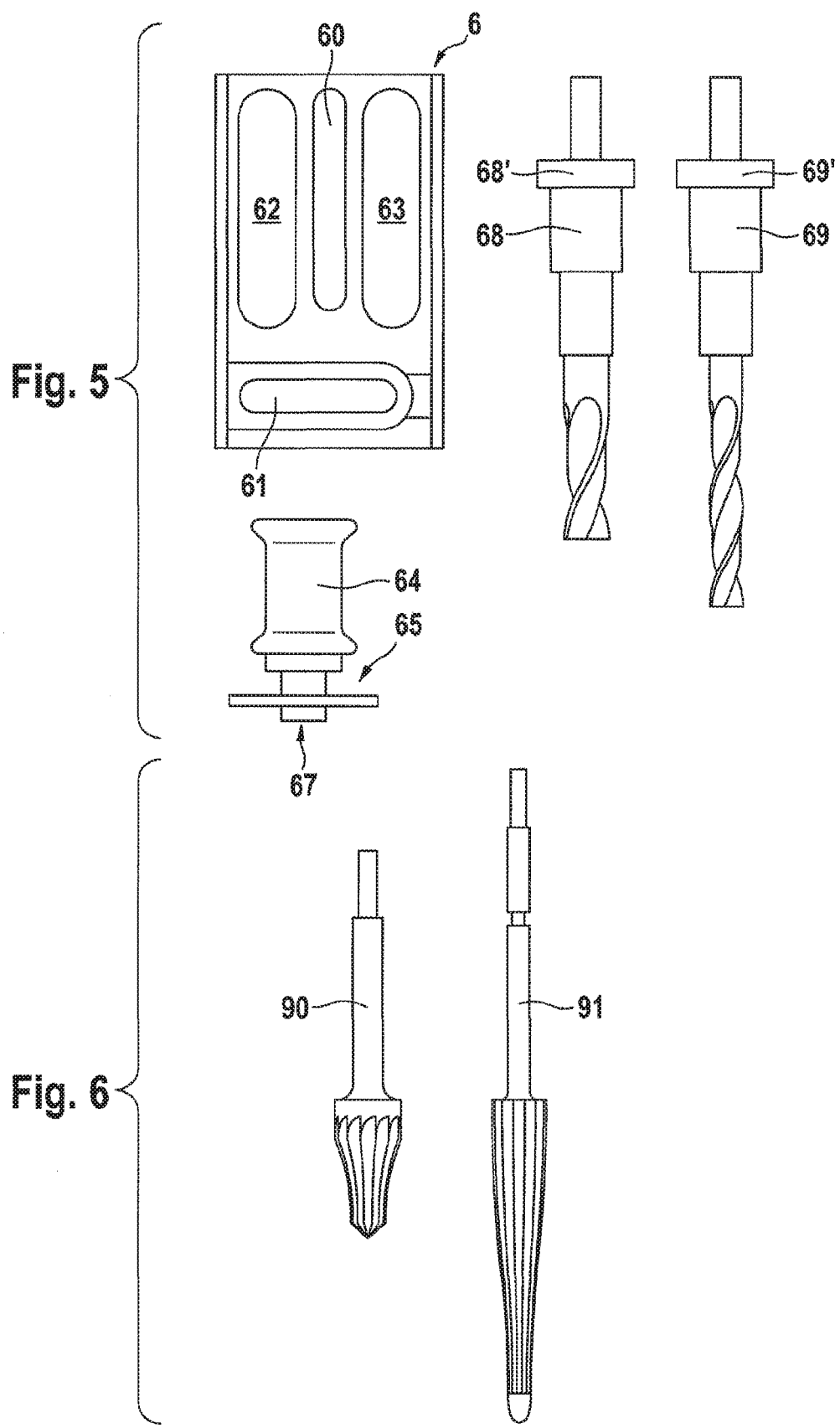

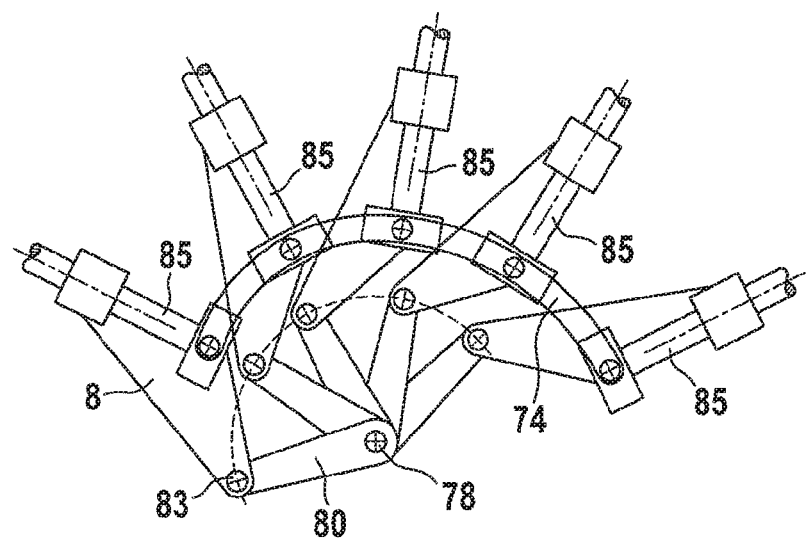
Fig. 12
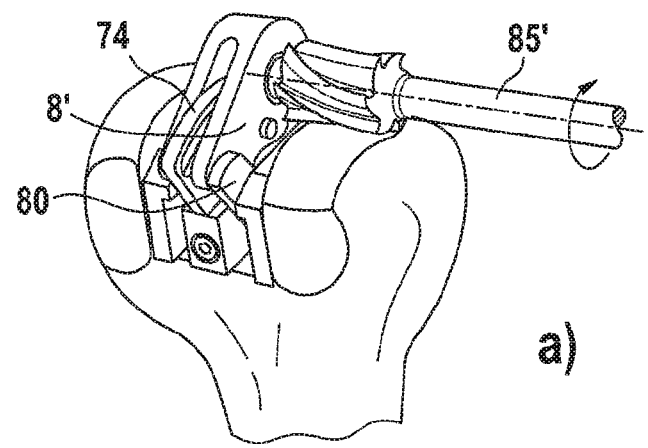
a)
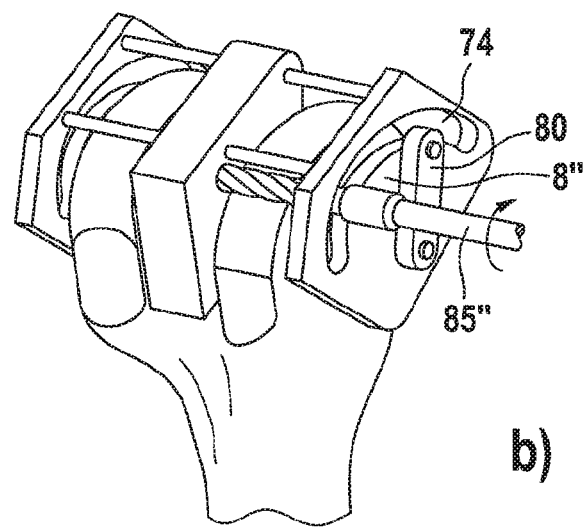
b)
Fig. 13

EQUIPMENT FOR INSERTING A JOINT PROSTHESIS, IN PARTICULAR A KNEE PROSTHESIS

REFERENCE TO RELATED APPLICATIONS

This application is a national stage application under 35 USC 371 of International Application No. PCT/EP2012/057163, filed Apr. 19, 2012, which claims the priority of European Application No. 11 163 566.0, filed Apr. 21, 2011, the entire contents of which are incorporated herein by reference.

FIELD OF THE INVENTION

The invention relates to a set of equipment for inserting a joint prosthesis, in particular a femur component of a knee prosthesis, at the end of a bone, in particular the femur.

BACKGROUND OF THE INVENTION

The implantation of a modern joint prosthesis, in particular a knee prosthesis, is a challenging task for the surgeon. Joint prostheses of this type have to reproduce the complex physiological path of movement of the natural joint in a highly lifelike manner. This requires not only highly developed prostheses, but also precise implantation of the joint prosthesis. Only in this way can it be ensured that the desired functionality of the natural joint can be correctly restored. It goes without saying that, to ensure sufficient success of the therapy, the prosthesis has to be positioned not only precisely, but also safely and reproducibly. In particular, the surrounding tissue, in particular surrounding bone material, must not be damaged or injured, since this tissue in many cases plays a significant role for the supporting function. Particularly in view of a long service life of the joint prosthesis, there is a conflict of objectives however. On the one hand, it is favorable for the long service life if forces are transmitted over a large area. On the other hand, a design with a large area that thus leads to dimensions of the prosthesis that are too large on the whole may result however in an increased spatial requirement and may therefore easily result in damage to surrounding tissue. There is thus a risk that material will be removed in incorrect areas in particular important for supporting the joint prosthesis. It is therefore necessary to carry out the implantation on the basis of exact position references.

The equipment known from the relevant prior art indeed enables tried and tested implantation of the joint prosthesis, in particular of a knee joint prosthesis. However, it presupposes considerable experience on the part of the surgeon, since the equipment itself only provides little assistance in respect of correct positioning.

SUMMARY OF THE INVENTION

In order to avoid harmful effects on the patient caused by erroneous positioning or by removal of too much natural bone substance, an object of the present invention is to create an improved set of equipment which enables more precise implantation.

This is achieved in accordance with the invention by a set of equipment as broadly described herein. Advantageous developments are disclosed in the detailed embodiments described below.

With a set of equipment for inserting a joint prosthesis, in particular a femur component of a knee prosthesis, at the end of a bone, in particular the femur, a base frame that has a guiding plate and a primary gauge protruding laterally therefrom, a fastening device for arranging the base frame on the bone in a fixed position, and a curved milling gauge with a main body and a guiding piece are provided in accordance with the invention, the guiding piece being movable along a curved guiding path relative to the main body and having a receptacle for an abrasive tool, and an aligning device, which places the curved milling gauge in a clearly defined relative position when the curved milling gauge is inserted into the base plate.

The invention is based on the concept of creating, by means of a base frame which is positioned in a manner known per se in a fastening device on the bone, a stable platform which is highly accurate by means of the aligning device and at which the curved milling gauge can be easily inserted and at the same time is aligned automatically and safely in a precise manner. The curved milling gauge has a curved guiding path, along which, by means of the abrasive tool, the bone can be shaped accordingly in a rounded manner. This is suitable in particular for preparation of a receiving seat for condyle components of the knee joint prosthesis. The complicated shape of these components can be produced easily and yet precisely by the surgeon thanks to the invention by means of a forced guidance, as is achieved in accordance with the invention by the curved guiding path of the curved milling gauge. Thanks to the forced guidance of the abrasive tool, deviations in the shape are hardly possible, even under unfavorable operating conditions. Not only is the prepared receiving seat thus created therefore highly accurate in terms of shape, but it is also ensured, with correct basic alignment of the base frame, which, via the aligning device, clearly determines the positioning of the curved milling gauge, that surrounding tissue is not injured or damaged, and in particular that no adjacent bone material is unnecessarily removed, which may be required to support the prosthesis. In particular, a wall-like bone residue can thus be left on the patella in the case of knee joint prostheses and not only provides a base for the patella-side support of the joint prosthesis, but also serves as a delimitation, acting frontally, of the box-shaped hollow of the medullary cavity for receiving the main body of the prosthesis.

In short, the invention, on the basis of a clean basic positioning, enables an exactly defined removal of bone material, wherein even complicated shapes, such as the varying curvature of the condyles in the case of a knee joint, can be developed easily and in a positionally accurate manner.

In particular for adaptation to the curvature of the condyles, which is not constant as already mentioned above, it is expedient if the curved guiding path of the curved milling gauge changes continuously in terms of its curvature along its extent. With such a change in curvature, the natural path of movement of the knee is reproduced as accurately as possible in terms of function. Here, the geometries are preferably selected such that the respective center of curvature remains in one plane over the non-constant curvature along the guiding path, wherein it shifts in a horizontal direction from front to rear (preferably by 10 mm, at most 20 mm). The generation of a complicated curve progression with varying curvature, wherein the position of the center of curvature is also to meet specific requirements, is difficult using the previous equipment and is hardly or even not at all assisted thereby. In this case, the focus in the prior art was rather on the experience and skill of the surgeon alone or primarily. With the equipment according to the invention, it is ensured that a precise shaping of the curve progression in accordance with the specifications can always be achieved.

In order to achieve this, the guiding piece, in which the abrasive tool is received, is expediently mounted both via a follower with the guiding path and via a pivot bearing pivotably on the main body. With this twofold mounting, both the rotation of the guiding piece along the guiding path is controlled, and also the alignment of the guiding piece relative to the guiding path. Both the radius of curvature and also the position of the center of the curvature can therefore be controlled precisely. It has proven to be particularly useful if the pivot bearing is arranged at a distance from the follower and has a toggle linkage mounted pivotably on either side. In this case, a space-saving kinematics is produced, which additionally combines precise guidance with an avoidance of cases of jamming. The latter in particular is a significant aspect, since blocking may easily occur in the operating environment, especially with highly precise, guided technical devices, due to the omnipresent risk of foreign body infiltration (in particular tissue residues or bodily liquids). The combination of a follower with a toggle linkage mounted pivotably on either side is robust in this respect.

It is particularly preferable if the toggle linkage is mounted removably on the main body via a securing device. This makes it possible to insert the curved milling gauge via its main body separately into the base plate, without this being impeded during this process by the guiding piece movable over a large adjustment range. This not only constitutes a simplification, but enables improved handling. This is true specifically also for the case when, due to low tolerances, the insertion of the curved milling gauge is difficult, wherein the force necessary for this purpose may be applied using a hammer where necessary. Thanks to the fact that the guiding piece can be removed, there is then no risk when the main body is driven in of damaging the guiding path of the guiding piece, which is key for accurate positioning.

In order to avoid a cumbersome assembly of the guiding piece in the operating environment and also to preclude the risk of a loss of individual assembly parts, a quick-action coupling is expediently provided between the guiding piece and main body. An embodiment as an angular lock, which can be separated by moving the guiding piece into an extension of the guiding path, has proven to be particularly expedient. In this case, an extension is understood to mean a region of the guiding path that is not necessary for the actual forming by means of the abrasive tool (but constitutes an additional region that is unused so to speak). By bringing the guiding piece into this extension, the angular lock reaches such a position in which it can be easily separated without tools. The same is true for the assembly process, which similarly can be carried out easily and without tools. For this purpose, the guiding piece needs to be brought merely into the extreme position in the extension so as to then be separated or refitted. In the region of the extension, this is expediently identified in that an opening of the guiding path outwardly is provided there. This opening is not absolutely necessary, but facilitates a removal of the guiding piece in this position. It goes without saying that this opening is not provided accordingly in the rest of the region of the guiding path belonging to the extension.

The angular lock may consist of a pivot bearing sleeve and a non-circular pivot pin, which is formed such that the angular lock opens only in one angular position of the guiding piece. This is achieved in that the pivot bearing sleeve is open toward one side via a constriction. The non-circular pivot pin is created such that it has different widths depending on positioning. This width in a specific positioning is referred to as the width in a specific meridian. If the non-circular pivot pin thus has such a shape that corresponds substantially to a rectangle with short circular-arc-shaped sides, the width in the meridian of smallest breadth is thus equal to the distance between the two long sides of the rectangle, and the width corresponding to the meridian of greatest breadth is equal to the length of the longer side of the rectangle plus the convex curvatures provided by the circular-arc-shaped short sides. Since the constriction is selected such that it is sufficient for the passage of the pivot pin in its meridian of smallest width, but is not sufficient for the passage in a meridian of greatest width, the guiding piece with its pivot pin can be removed merely in one such orientation in which the pivot pin can pass the constriction with its meridian of smallest width. In accordance with the invention, this is then only the case when the guiding piece is located in the position of the guiding path which belongs to the extension. In the other positions on the guiding path, the guiding piece is locked, since there the width of the pivot pin is greater than the breadth of the constriction, such that the pivot pin cannot be removed through the constriction. A simple and robust quick-action coupling, which is controlled in an angle-based manner and therefore provides the guarantee that the separation can only occur in one specific position, is thus produced. The guiding piece is likewise assembled easily, since it only has to be inserted in the correct position into the extension of the guiding path, wherein the pivot pin with its meridian of smallest width is readily guided through the constriction into the pivot bearing sleeve. A simple locking mechanism, without tools, is thus achieved by inserting the guiding piece into its position.

The toggle linkage is preferably likewise removably mounted on the main body. It is thus made possible to remove all movable parts. This is not only favorable for the cleaning of the equipment, but also, as already mentioned, for the assembly of the main body in difficult cases, without resulting in damage to the sensitive guiding devices. The toggle linkage is preferably mounted via a securing device, such that it is protected against unintended detachment from the intended position. In particular, a screw has proven to be an expedient securing device.

By means of its mounting, the guiding piece movable along the guiding path defines an axis for the abrasive tool. The axis can be oriented such that it is arranged in the pivot plane of the guiding piece, but is preferably at an oblique angle. This axis is further preferably likewise arranged at an oblique angle to the line between follower and pivot bearing. For this purpose, a range between 10° and 35°, further preferably between 15° and 30°, has proven to be expedient. A bend reserve is thus created at the toggle linkage and also allows continuous change of the radius along the course of the guiding path.

The receptacle for the abrasive tool on the guiding piece preferably cooperates with a depth stop. In this case, a depth stop is understood to mean a device which delimits the penetration depth of the abrasive tool into the workpiece, that is to say in this case the bone on which the equipment according to the invention is used. An embodiment of the depth stop in such a way that it is a stepped seat, which is preferably open toward one side, has proven to be expedient. As a result of the graduation, a thickening arranged accordingly on the deep miller rests thereon and thus forms a stop with respect to the penetration depth of the supporting tool. The lateral opening ensures that the abrasive tool can be inserted into the receptacle directly from the side, without having to be threaded in a cumbersome manner.

In principle, it is indeed sufficient to provide just one receptacle on the guiding piece, however it is advantageous particularly for knee prostheses if a double receptacle is formed on the guiding piece in order to form two condyles. The abrasive tool can thus be changed over once one condyle is formed in order to thus form the second condyle at the other position. A disassembly or a changeover of the curved milling gauge is therefore not necessary, and therefore the precise positioning is maintained.

It has proven to be expedient if the double receptacle is formed on the guiding piece such that divergent axes are produced. In this case, divergent is understood to mean that the cutting head of the abrasive tool points outwardly in the inserted state. The condyles can thus be provided with a physiological inclination, which assists a self-centering function present in the natural knee joint.

The double receptacle is not absolutely necessary however. It may also be possible to disassemble the guiding piece with the pivot bearing, and where applicable, with the toggle linkage from one side of the main body and to reassemble it on the other side. The condyle can thus be prepared initially on one side, and, after reassembly on the other side with the same receptacle on the guiding piece, the other condyle can be prepared. Since in this case the positioning of the curved milling gauge with its main body also does not have to be changed per se, the precise positioning is maintained.

Fastening bores are expediently provided on the main body and/or the guiding path. They enable a securing of the positioning of the curved milling gauge, more specifically independently of its entry into the base plate. The fastening security and therefore ultimately also the quality of the positioning accuracy are therefore increased; in particular it is made possible to remove the base frame.

In accordance with a specific aspect of the invention, which may also be worthy of independent protection, various inserts for the base frame are provided. An aligning insert may thus be provided exchangeably on the base frame, said aligning insert being designed to receive an aligning body in a defined position. The aligning body may in particular be a bone broaching tool, in particular an awl or a rasp for opening the medullary cavity.

The guiding piece described in previous paragraphs is usually formed such that the axis of the receptacle for the abrasive tool is oriented such that the axis has a radial orientation. This means that it is directed substantially toward the center of curvature. Alternatively, the axis may also be oriented transverse to the plane defined by the curvature. This provides the advantage that the abrasive tool can be inserted into the receptacle from the side. With a sufficiently large abrasive tool, two condyle shapes can thus be formed on a femur with a movement along the guiding path. However, a variant is preferred in which the guiding piece with the pivot bearing and, where applicable, the toggle linkage can be disassembled from one side of the main body and reassembled on the other side. In this case, the abrasive tool is dimensioned such that only one condyle path, specifically the closest, is formed. This provides the advantage of more precise control and also makes it possible to provide an inclination due to a possibly slightly tilted axis in the receptacle of the guiding piece of the condyle path. A result comparable to that which can be achieved with the divergent axes in the above-described guiding piece having a double receptacle is thus obtained.

In order to achieve an independent fastening of the curved milling gauge to the bone to be machined, fastening bores may expediently be provided on the main body and/or the guiding path. They are used primarily as a replacement for the fastening by means of the orienting device to the base frame anchored in the bone, such that the base frame can be removed as required.

In accordance with a further aspect of the invention, which may be worthy of independent protection, an ensemble of inserts are provided for the base frame and can be received exchangeably in the guiding plate. In this case, the inserts may be formed in particular by an aligning insert, a frontal-sawing insert, a first milling insert, a second milling insert, and a third milling insert with a slotted link guide.

The aligning insert is designed so as to be arranged exchangeably in a defined position on the guiding plate and has a receptacle for the aligning body. The base plate can therefore be clearly positioned with respect to the aligning body. The aligning insert is expediently side-dependent, that is to say there is an aligning insert "L" for implantation of the left-side prosthesis and an aligning insert "R" for the implantation of a right-side prosthesis. It is noted that a symmetrical auxiliary aligning insert, which can therefore be used similarly on either side, may also be provided additionally as supplements.

The receptacle for the aligning body on the aligning insert is expediently open on one side. This is preferably implemented by means of a constriction. The aligning body (this generally being here an implement inserted into the medullary cavity of the bone, such as an awl or a milling cutter) can thus be easily inserted into the receptacle and removed therefrom from the side.

The ensemble of inserts further comprises a frontal-sawing insert. This has two kerfs aligned in a V-shape relative to one another and a bipolar fastening. The bipolar fastening is understood to mean a fastening which defines two alternative fastening positions. These fastening positions are selected such that the kerfs are arranged in one case for implantation of a left-side prosthesis and in the other case for implantation of a right-side prosthesis. An expedient embodiment for such a bipolar fastening may be two individual fastening bores, or preferably a slot, of which the end points define the respective bipolar fastening positions.

The set of equipment preferably comprises further spacers for different heights, which are designed for arrangement on either side at the edge of the guiding plate. A specific distance of the guiding plate from the bone can be adjusted by means of the spacers. This is suitable in particular for cases in which bone material has already been removed due to a prior operation. It is thus possible to compensate for the material loss. Spacers having different dimensions are preferably contained in the set of equipment.

The ensemble further comprises a first milling insert, which can be attached exchangeably in the guiding plate. It forms a defined receptacle for a broach milling cutter, said receptacle preferably also forming a depth stop for the broach milling cutter. It is thus ensured that the milling process is carried out in a precise manner. In particular, the broach milling cutter therefore does not drift to the side and therefore remove bone material laterally or frontally or dorsally in an undesired manner. The depth stop further ensures that bone material is removed only in the depth necessary for implantation. The distance between the receptacle and the primary gauge is dimensioned such that, when the broach milling cutter is inserted, a distance remains which corresponds to the thickness of a wall that is to be left on the frontal side of the patella. This is achieved thanks to the forced guidance thus achieved of the broach milling cutter, even in a confusing operating environment, more specifically including a less experienced surgeon.

The set of equipment preferably further comprises a feeler gauge, which can be attached at a precise angle to a plug receptacle on the base frame. The position of the pivot point of the prosthesis can be indicated by means of this feeler gauge, more specifically preferably in two orientation planes.

The ensemble further comprises a second milling insert, which can be attached exchangeably to the guiding plate. This has a double receptacle for receiving a bulk milling cutter in a manner in which the cutter can be plugged into either receptacle. In this case, the double receptacle is preferably formed such that it has different depth stops and additionally a lateral offset. In this case, a lateral offset is understood to mean that the bulk milling cutter, in one position of the double receptacle in the lateral/medial direction, is positioned differently than in the other position of the double receptacle. The same is true with respect to the depth stop, specifically the fact that the bulk milling cutter, in one of the two positions, reaches a greater milling depth than in the other position. The double receptacle is preferably formed such that its regions overlap. After the milling process, an associated hollow is thus produced in the bone. This forms the basis for further development so as to be able to produce a defined shape for precise implantation. A space of maximum size can therefore be milled out without at the same time posing the risk of injuring the surrounding bone wall.

It is noted that an auxiliary milling insert which likewise has a double receptacle may also be provided as a second milling insert. This double receptacle is simplified however in the sense that it preferably has stops of identical depth and/or has no lateral offset. Simpler structures for the hollow can therefore be produced. This auxiliary milling insert is then in particular expedient if only a relatively small hollow has to be developed.

The ensemble further comprises a third milling insert, which can be attached to the guiding plate. This forms a slotted link guide for a depth milling cutter, which is preferably received in a slotted link slider. With the slotted link guide, the hollow can be formed finely by means of the depth milling cutter. The slotted link in this case delimits the movement of the depth milling cutter in the lateral/medial direction. Furthermore, the movement of the milling cutter in the frontal/dorsal direction is limited by means of a slotted link window. The slider preferably has a handle, which surrounds the depth milling cutter coaxially. The depth cutting miller can therefore be guided more precisely. The slotted link guide may further have windows in order to visually check the milling process.

The slotted link guide preferably has a depth stop. A second depth milling cutter may thus also be provided, such that two different milling depths are defined. This enables safe and more precise development, even of complex hollows.

In accordance with an alternative embodiment, the slotted link guide may also comprise two guiding levers connected to one another in a hinged manner. In this case, the receptacle for the depth milling cutter may be arranged at one end, whereas a pivotable mounting on the insert in the guiding plate is provided at the other end of the guiding levers interconnected in a hinged manner. The milling cutter is thus guided more precisely in the sense of a forced guidance. Furthermore, this embodiment may have an advantage that a risk of canting is reduced. The mounting on the insert is expediently designed such that the guiding levers connected in a hinged manner can only be fitted and separated if the milling tool implement is not inserted.

An insertion guide is preferably provided on the guiding plate and is formed in particular as a dovetail guide. The different inserts of the ensemble as have been described beforehand, can therefore be inserted easily and positioned precisely with respect to the guiding plate.

The set of equipment advantageously further comprises a pair of insertion tongs for the curved milling gauge. These tongs grip the curved milling gauge with a form fit in a defined position, the pair of insertion tongs cooperating via aligning lugs with the aligning device such that the insertion tongs have a clear position and therefore the curved milling gauge held with a form fit in a clear position by the insertion tongs is also positioned clearly relative to the guiding plate. The handling is thus simplified considerably, since the curved milling gauge having generally relatively large dimensions can thus be positioned safely and precisely. An incorrect positioning is therefore ruled out.

The set of equipment expediently further comprises aligning rods for lateral arrangement on the base frame in such a way that they point away from one another. Aligning bores are provided on lateral sides of the base frame for assembly of these aligning rods.

The set of equipment further comprises a drill having a depth stop. It is designed to create receptacles on the bone in a positionally accurate and simple manner, said receptacles being intended for anchoring pins of the endoprosthesis.

The set of equipment further comprises various awls for broaching a concavity on the bone, in particular a medullary cavity on the femur. It expediently further comprises a rasp/broaching awl, of which the shaft has a recess. This is formed so as to receive a stop plate, which in particular acts as a depth stop. The rasp/broaching awl is expediently designed such that it has 2, 3 or 4 cutting edges. In this case, the teeth are arranged on the cutting edges with a vertical offset relative to one another. As the teeth are rotated, bone material is thus removed at various points, such that the bone surface is smoothed.

The set of equipment expediently further comprises a direction gauge, which is provided for positioning of the base plate and which acts on the aligning device. In particular, it is designed to act on the rasp/broaching awl inserted in the medullary cavity, and therefore to position the base plate exactly with respect thereto.

BRIEF DESCRIPTION OF THE DRAWINGS

The invention will be explained in greater detail hereinafter with respect to the accompanying drawings, in which an advantageous exemplary embodiment is illustrated and in which:

FIG. 1 shows an illustration of a base frame;
FIG. 5 shows a slotted link milling gauge for fine machining the hollow;
FIG. 6 shows tools for preparing a medullary cavity.

FIG. 12 shows an illustration of the kinematics of the guiding piece on the main body;

FIG. 13 shows alternative embodiments of the guiding piece;

DETAILED DESCRIPTION OF THE INVENTION

Figure 2:
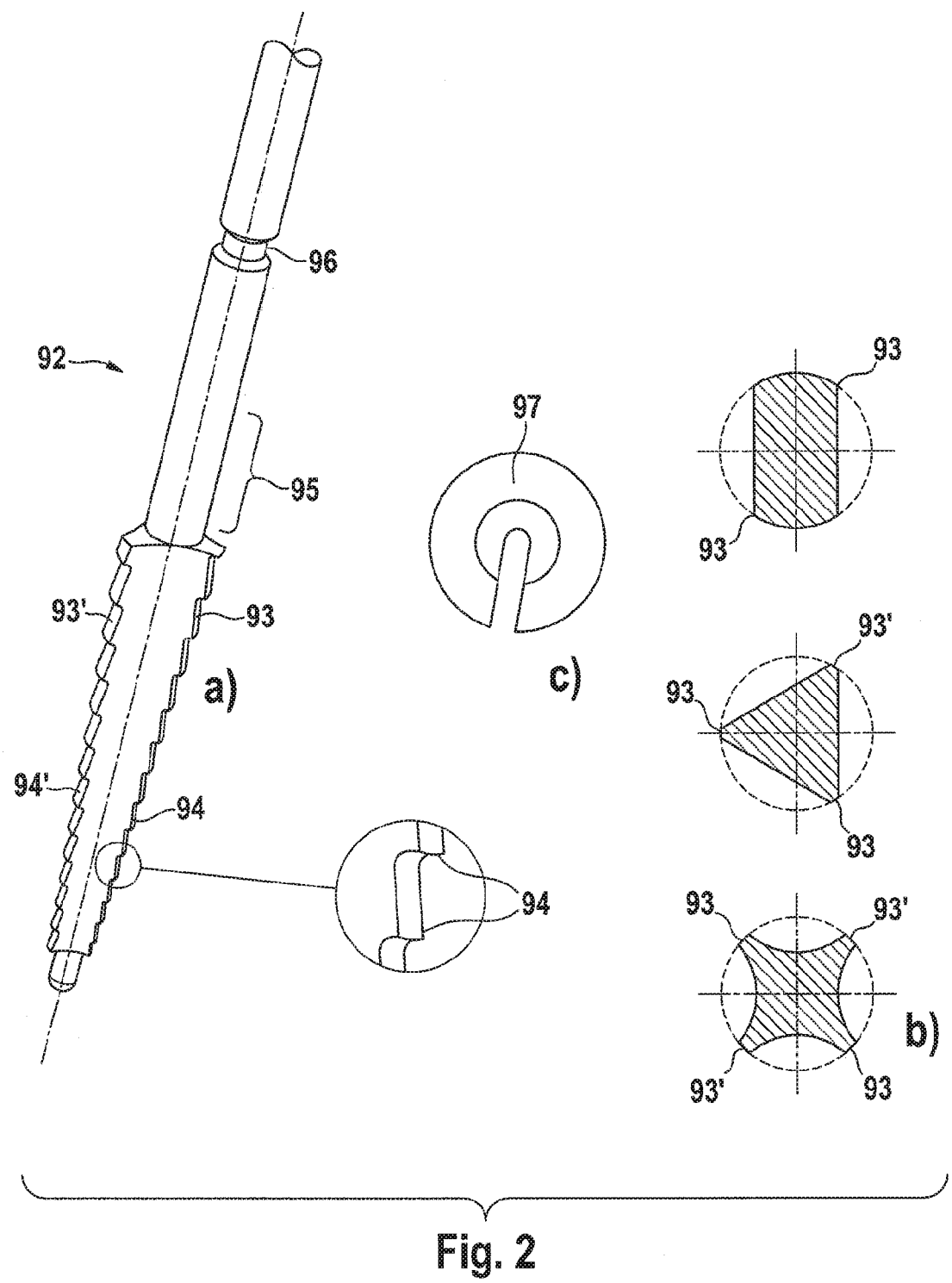
FIG. 2 shows a reamer.
Figure 3:
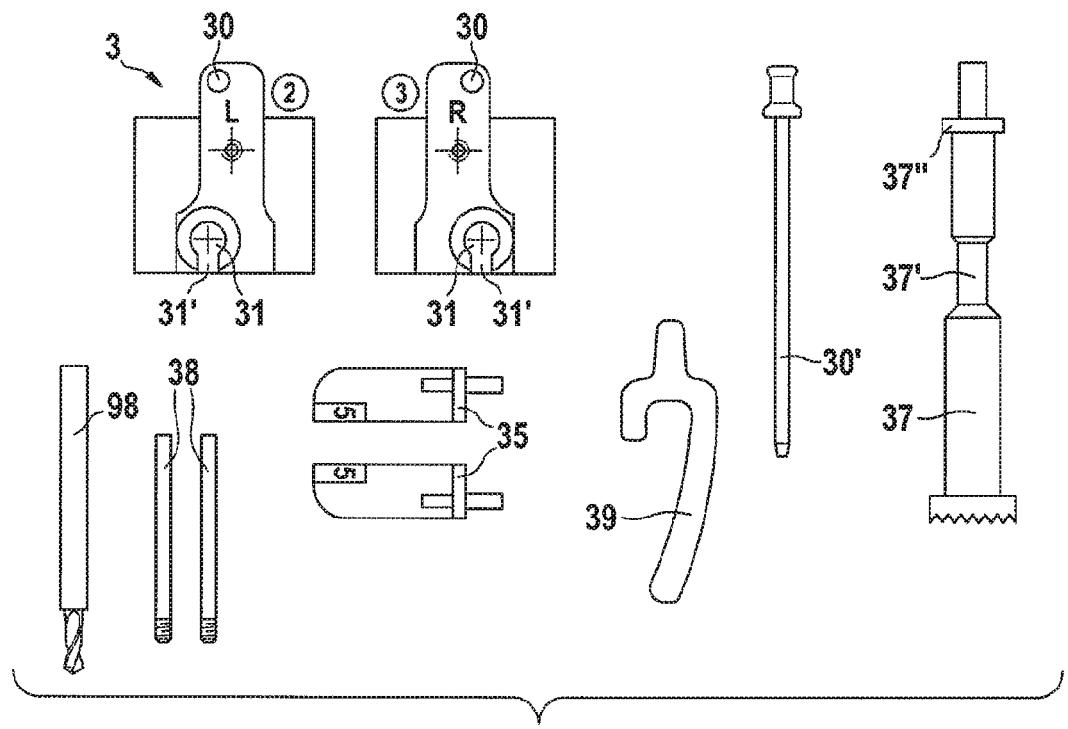
FIG. 3 shows elements for aligning the base frame.
Figure 4:
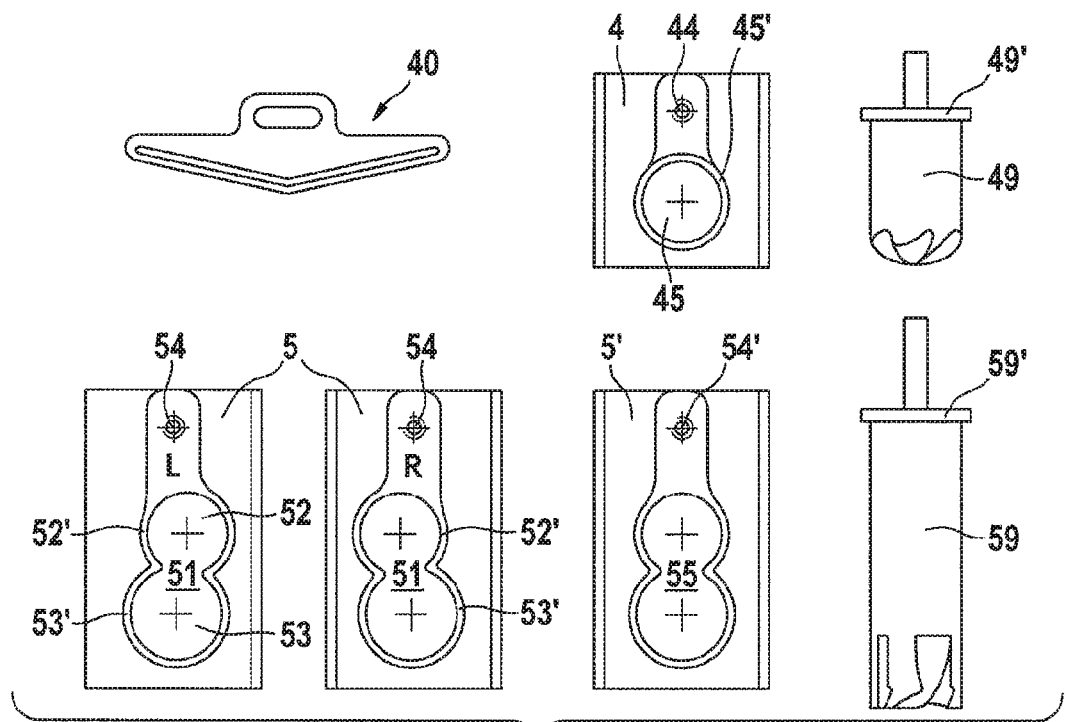
FIG. 4 shows sawing and milling gauges for preparing a hollow at the end of a femur.

The set of equipment illustrated as an exemplary embodiment in FIGS. 1-11 for implanting a knee joint endoprosthesis comprises two awls 90, 91 (see FIG. 6) and a rasp/broaching awl 92 (see FIG. 2), a base frame 1, pins 99 as a fastening device for fastening to a femur bone, an aligning insert 3, a frontal-sawing insert 40, spacers 34, a feeler gauge 39, a first milling insert 4, a second milling insert 5, a third milling insert 6 as a slotted link guide, and a curved milling gauge 7 with a condyle milling cutter 85.

The base frame 1 comprises a guiding plate 12 and a primary gauge 11 protruding orthogonally laterally therefrom. A first saw blade guide 20, which is used to compensate for different condyle heights, is formed on the primary gauge 11 in the upper region, and a second saw blade guide 21, which is used to machine the condyles with use of femoral segments, is formed on the primary gauge 11 in the lower region. Furthermore, bores 22 for fastening pins are formed in the region between the saw blade guides. In the region of transition to the guiding plate 12, receiving bores 26 for spacers are provided, aligned in the direction of extension of the guiding plate 12.

The base frame 1 is provided in different sizes. In this case, the distance between the reference plane 10 and the saw blade guides 20, 21 and also the receiving bores 26 for the spacers is identical for the different sizes.

The guiding plate 12 is formed with its underside as a reference plane 10. This serves as a bearing surface for condyles of the femur. A planarity is formed on the upper side and acts as a tool plane 14. It is the reference plane for the different inserts that are received on the guiding plate 12. In this case, the dimension between the reference plane 10 and the tool plane 14 is matched to the respective size of the implant to be inserted. A linear guide 2 is arranged on either side of the tool plane 14 and comprises two undercut edges between the tool plane 14 and the upper side of the guiding plate 12. These act as a dovetail guide for the inserts 3, 4, 5 and 6.

A milled recess 15 is formed on the guiding plate 12 on each of the lateral sides. It is of such a depth that the breadth remaining between said milled recesses corresponds to the width of the width dimension of the implant associated with the respective base plate 1. The milled recess 15 thus acts as a visual aid for selecting the implant sizes. An aligning bore 23 with an inner thread, which indicates the position by means of an aligning rod 38 to be screwed in, is provided in each milled recess 15. Bores 28 for fastening pins 99 are provided in a manner flanking the milled recesses 15. In the central region of the guiding plate 12, a central opening of an approximately rectangular basic shape is formed, which on its two lateral faces pointing to the side acts as a lateral delimitation 66 and by means of its edge 65' facing away from the primary gauge acts as a rear delimitation for a milled mortise recess. Guiding slots 17 for an insertion implement 75 of the curved milling gauge 7 are formed in the lateral sides 66. Drill guides 18 for a pin-hole drill are provided on either side in the guiding plate 12 adjacently to said guiding slots. A posterior saw blade guide 19 for condyle machining is formed in the rearward region in the vicinity of the rear delimitation 65' for the milled mortise recess. At the opposite end of the large central opening, a diagonal changeover guide 16, 16' is formed in the end pointing toward the primary guide 11 and is oriented parallel thereto. At its respective side faces, said changeover guide has a double curve shape and thus forms a bipolar receptacle for the frontal-sawing insert 40. This is inserted in the position denoted by reference numeral 16 for processing for a left-side position, and is inserted in the positioning denoted by reference numeral 16' for machining of a right-side implantation.

A central fastening 14 is provided centrally on the base plate 12 above the primary gauge 11. Said fastening is used to fasten the individual inserts. It is always located at the same point on the base frame 1 for the different sizes, such that the different inserts can be used without difficulty with base frames of different size. Free spaces 29 are formed on either side thereof and create the necessary clearance for fastening pins on the curved milling gauge 7 for fastening thereof to the femur.

The rasp/broaching awl denoted in its entirety by reference numeral 92 comprises a plurality of cutting edges 93 in its lower region, which are each provided with a multiplicity of teeth 94. A tooth-free region 95 with reduced diameter upwardly adjoins the cutting edges 93 provided with the teeth 94. A recess is formed thereabove. This recess serves as a receptacle for a stop plate 97. The cutting edges 93 are preferably formed in a triangle configuration, which means that three cutting edges 93 are provided, which are arranged at an angular distance of 120°. It is noted that a different number of cutting edges, in particular two cutting edges or four cutting edges, could also be provided (see illustrations in FIG. 2b). In the embodiment illustrated in FIG. 2a, the arrangement of the teeth 94 is selected such that the teeth 94 of a cutting edge 93 are arranged so as to be offset vertically in relation to the teeth 94' of the adjacent cutting edge 93', as measured from the tip of the rasp/broaching awl 92. This has the advantage that, as the rasp/broaching awl 92 is rotated, a more uniform shaping of the bone wall is achieved. It is specially designed to preserve the bone in the region close to the edge. For this purpose, it has a flattened portion, with which it is oriented relative to the bone edge. After introduction into the depth of the medullary cavity and after rasping, it is then used as a reamer.

Figure 14:
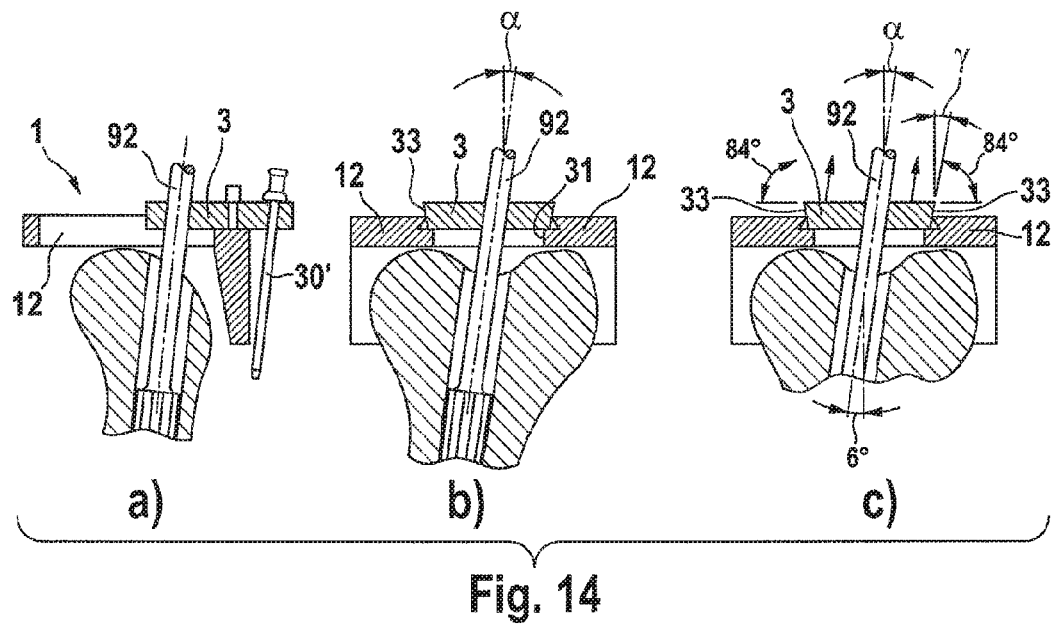
FIG. 14 shows details for aligning the base frame.

The rasp/broaching awl 92 acts via its upper shaft region above the recess 96 as an aligning aid and cooperates with the aligning insert 3 for this purpose. This insert has an opening 31, which is open toward the side via a constriction 31'. The rasp/broaching awl 92 can be introduced via its recess 96 into the opening 31 by being inserted through the constriction 31'. A relative positioning between the rasp/broaching awl 92 and the base plate 1, in which the aligning insert 3 is inserted, is thus achieved. The aligning rods 38 are screwed into the aligning bores 23 and in doing so indicate to the surgeon the position of the base frame and thus act as an aligning aid. In the illustrated exemplary embodiment, the opening 31 is not oriented orthogonal to the reference plane 10, but is arranged at an oblique angle thereto. The deviation from the orthogonal direction is denoted as a shaft angle $\alpha$ and is a characterizing dimension for the prosthesis (in the example 6 degrees). In order to allow the surgeon to visualize this shaft angle, an opening 30 is also formed on the aligning insert 3 and is formed on a pair of tongs protruding via the front delimitation of the base plate 1, a tracer pin 30' being plugged through this opening 30, being arranged outside the femur to be machined, and therefore indicating to the surgeon the shaft angle of the rasp/broaching awl 92 inserted in the medullary cavity of the femur to be machined (see FIGS. 14b and c).

The aligning insert 3 is chamfered in a wedge-like manner on its lateral sides 33 (wedge angle $\gamma$ is 4 to 10 degrees, preferably 6 degrees), more specifically at least by the shaft angle $\alpha$. On the one hand, sufficiently accurate positioning in the linear guide 2 is thus achieved, and on the other hand, unlike with an actual dovetail guide, the insert can be removed upwardly, more specifically at the end of the aligning process (see FIG. 14).

Figure 16:
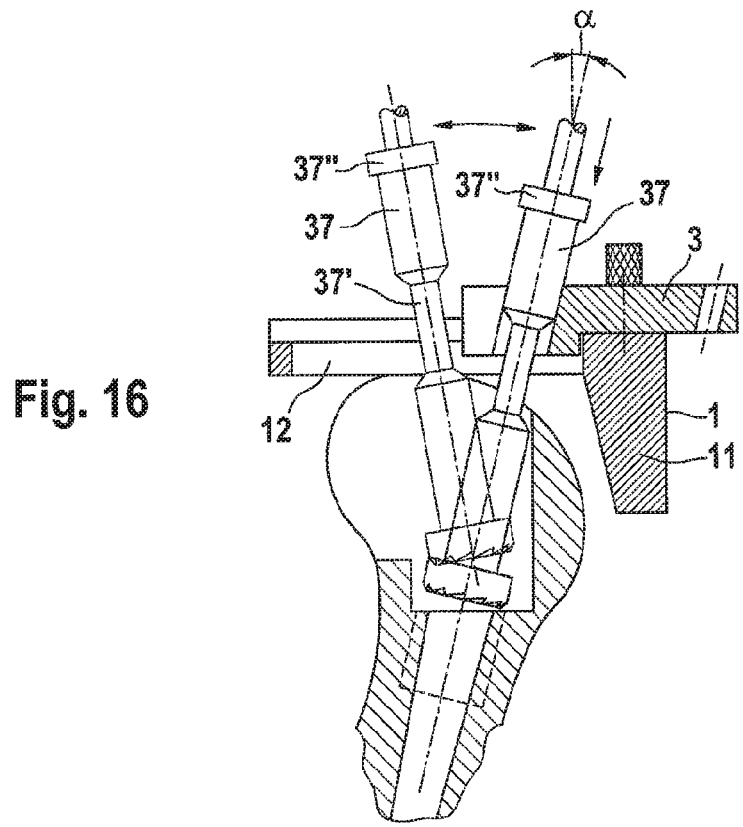
FIG. 16 shows details for use of the milling cutter according to FIG. 3.

It is noted that a concavity can be premachined in the medullary cavity of the femur using a broach milling cutter 37, which may possibly have a recess 37', similarly to the recess 96 on the rasp/broaching awl 92, and can be inserted accordingly via the constriction 31' into the opening 31 (see FIG. 16). The broach milling cutter 36 is in this case tilted by the same shaft angle $\alpha$ as the rasp/broaching awl 92. It is thus made possible to mill out a deep region for the shaft of the prosthesis. The maximum milling depth is limited in this case by a depth stop 37" formed as a shaft collar. The required erosion can thus be produced even deep in the bone, more specifically at the correct angle, without the need for specific skills on the part of the surgeon for this purpose.

Figure 15:
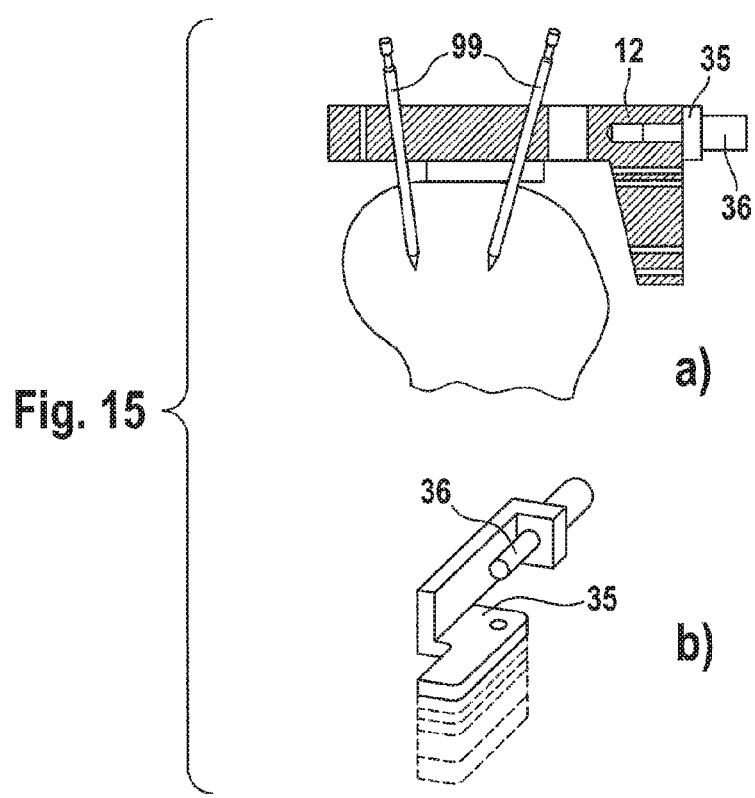
FIG. 15 shows details for use of compensating pieces according to FIG. 3.
Figure 17:
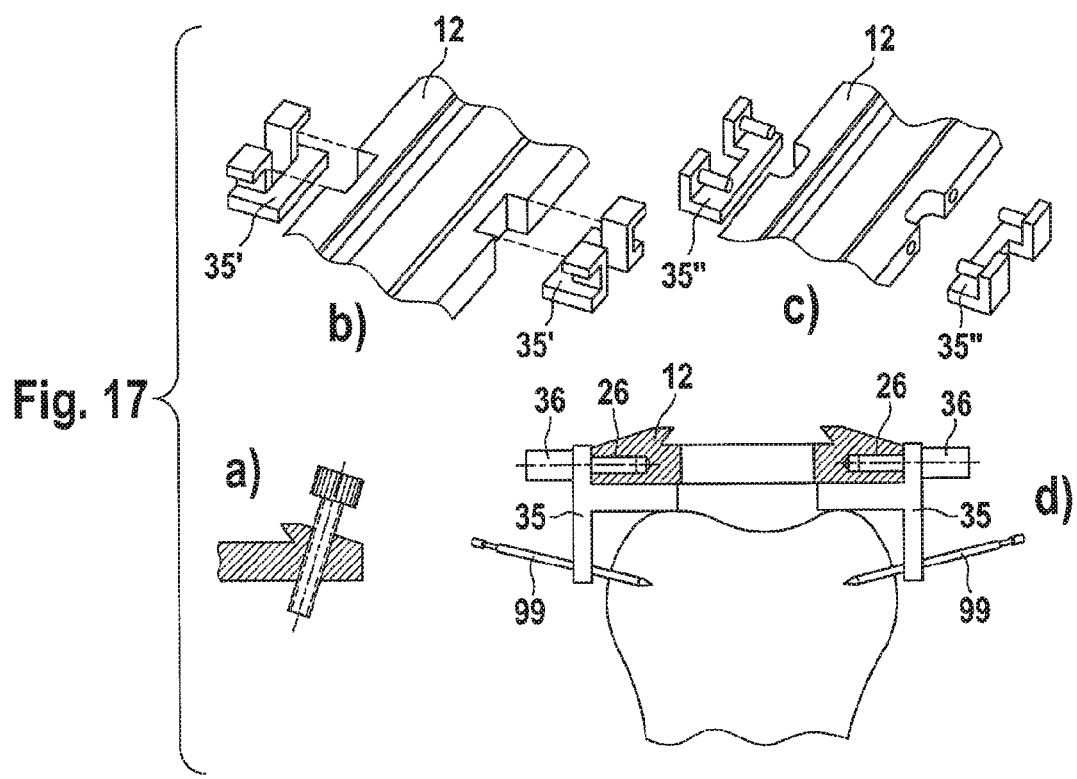
FIG. 17 shows an alternative fastening of the spacers.

Generally, the base frame 1 will rest directly via its reference plane 10 on the end of the femur. This is not always the case however, but in particular in cases of reoperation and in other cases, in which bone material is already absent (if it was removed in a previous operation or is absent due to a defect), spacers 35 can be arranged on the underside 10 of the base plate 1 (see FIG. 3). These are formed in pairs and are held via fastening pins 36, which are inserted into the receiving bores 26, on the primary gauge 11 of the base plate 1 (see FIG. 15a). They are available in different thicknesses (see FIG. 15b), such that a fine adjustment can be made herewith. Alternatives for the spacers are illustrated in FIG. 17. The simplest alternative consists in arranging adjusting screws at the edge of the base frame (see FIG. 17a). Alternative spacers 35, 35' for forming a base may also be provided and are held with a form fit on the lateral sides via hook connections or pin connections (see FIGS. 17b and c). These spacers may also be provided in the lower region with pin openings through which fastening pins 99 are inserted (see FIG. 17d).

If the position of the base frame 1 is then defined by means of the aligning insert 3, the base frame is thus fixed relative to the femur by introducing the fastening pins 99 into the openings 28. The aligning insert 3 and the rasp/broaching awl 92 can then be removed. The aids used for positioning, in particular the aligning rods 38 and the tracer pin 30', are likewise removed.

Figure 18:
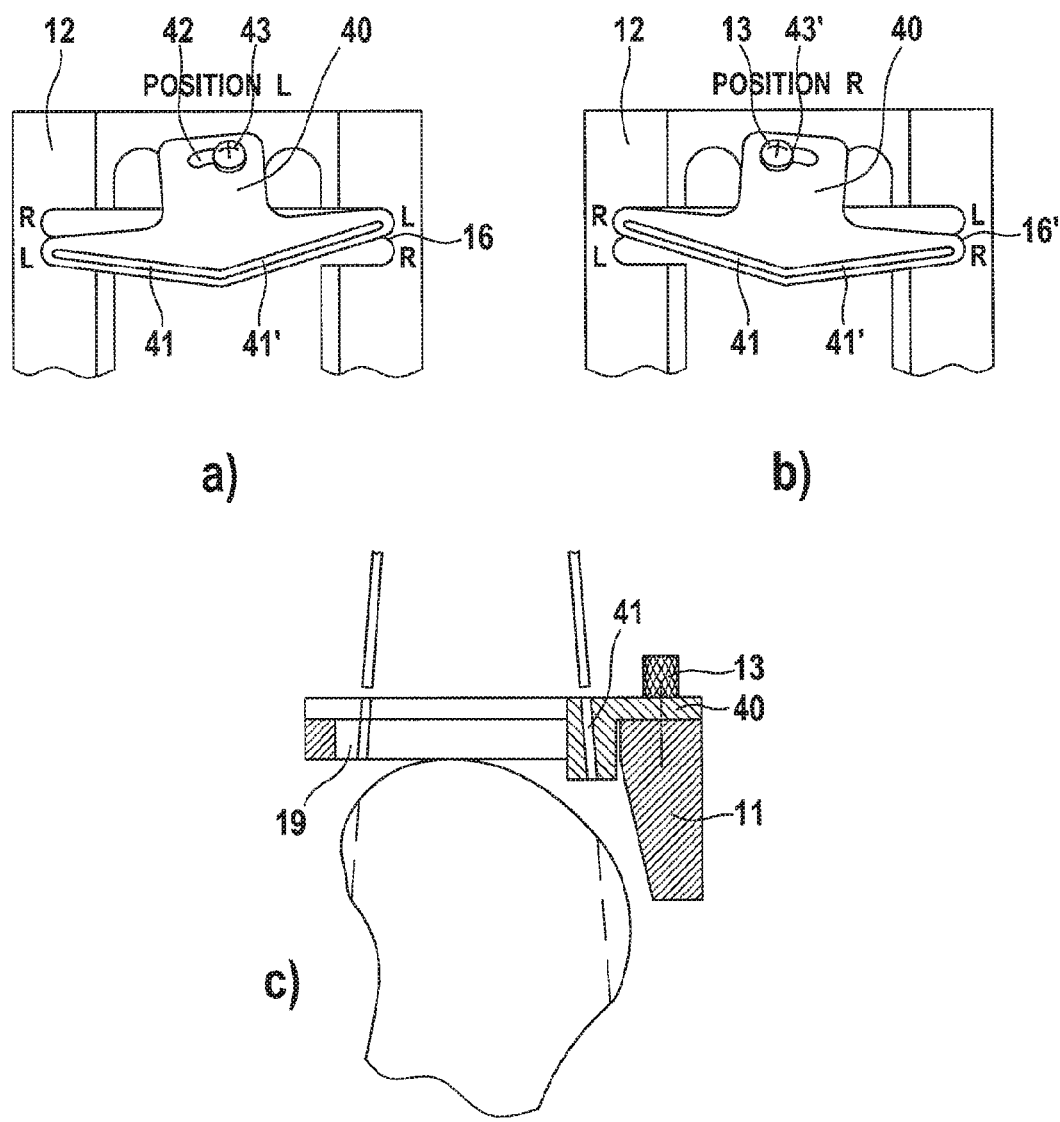
FIG. 18 shows details for use of the sawing gauge according to FIG. 4.

By means of a bone saw known per se and not described in greater detail, the condyles at the dorsal end can then be machined with use of the posterior saw blade guide 19 (see FIG. 18c). In the next step, the frontal-sawing insert 40 is inserted into the corresponding diagonal changeover guide 16, 16', more specifically irrespective of whether the implantation is a left-side or right-side implantation. The orientation given by the double arc-shaped recess 16, 16' is defined by the bipolar fixing by means of the slot 42, in each of the end positions 43, 43' of which a fastening screw 13 is screwed into the central fastening 14. The frontal condyle side is then machined along the V-shaped saw blade guides 41, 41' by means of the bone saw known per se (see FIGS. 18a, b).

Figure 19:
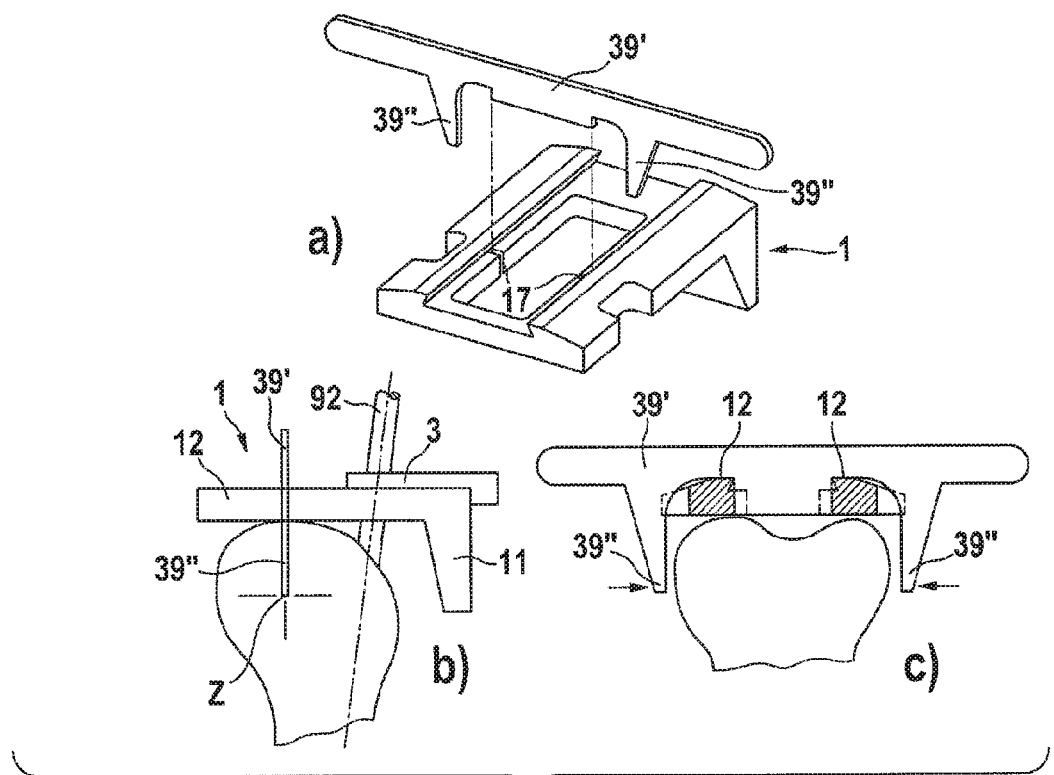
FIG. 19 shows an alternative embodiment of the direction gauge.

In the next step, the plane of rotation can then be fixed in one direction by means of the feeler gauge 39, which is plugged into the slot 27 on the base frame 1, and the plane of rotation in another direction, oriented transverse to the first-mentioned direction, can then be fixed by insertion into the sawing slot 40, 40'. The pivot point is determined by the point of intersection of the planes of rotation. An alternative implement is illustrated in FIG. 19. It comprises a bridge support as a direction gauge 39' with indexings 39" arranged on either side. The bridge support 39' is inserted into receiving slots 17 on the base frame 1, and the orientation of the base frame 1 can be set by the form-fitting connection thus produced. The length of the indexings 39" is dimensioned such that they indicate via their end the respective resulting position of the pivot point Z (see FIGS. 19b and c). This enables quick alignment that can be easily checked.

Figure 20:
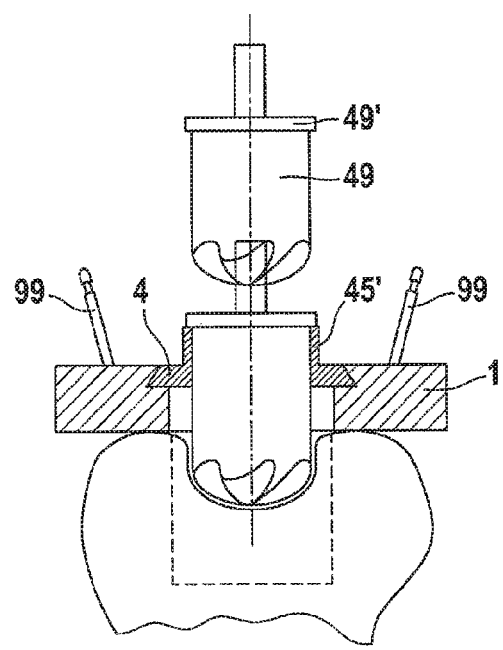
FIG. 20 shows a front view for use of the first milling gauge with milling cutter according to FIG. 4.
Figure 21:
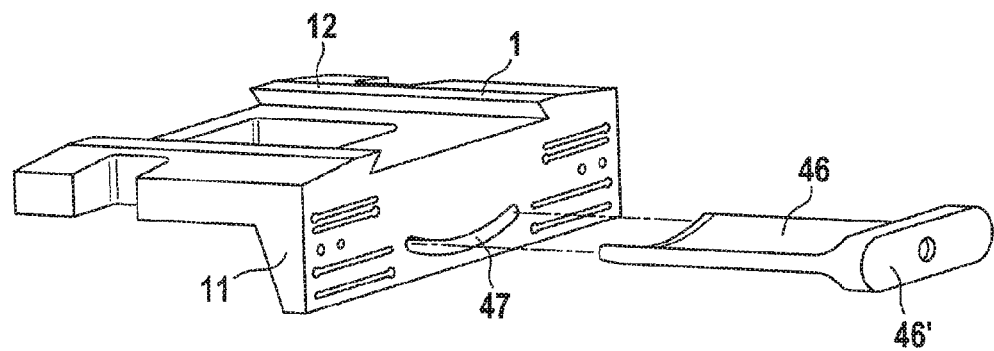
FIG. 21 shows an alternative for use of the first milling cutter.

In the following step, the first milling insert 4 is inserted into the base frame 1 and is fixed by means of the central fastening 14, which is accessible through an opening 44, and by means of the fastening screw 13. The insert 4 has a large central opening 45 with an upwardly protruding guiding sleeve 45' which form a receptacle for a broach milling cutter 49. This has a collar 49' in its upper region, said collar cooperating with the upper edge of the guiding sleeve 45' in such a way that a depth stop for the broach milling cutter 49 is formed. Part of the concavity in the medullary cavity necessary for implantation is thus created, and on the other hand the wall left by the reamer is reduced in the front region, defined in terms of its height (see FIG. 19). The reduction of the height of the wall in the front region can alternatively also be achieved by means of a chisel 46, as illustrated in FIG. 20. The chisel 46 has a main body which, in cross section, has the shape of a segment of a circular arc and, at the rear end, has an impact head 46' also acting as a depth stop. A guiding slot 47 complementary to the cross-sectional shape of the chisel 46 is provided in the base frame 1 on the primary gauge 11.

Figure 22:
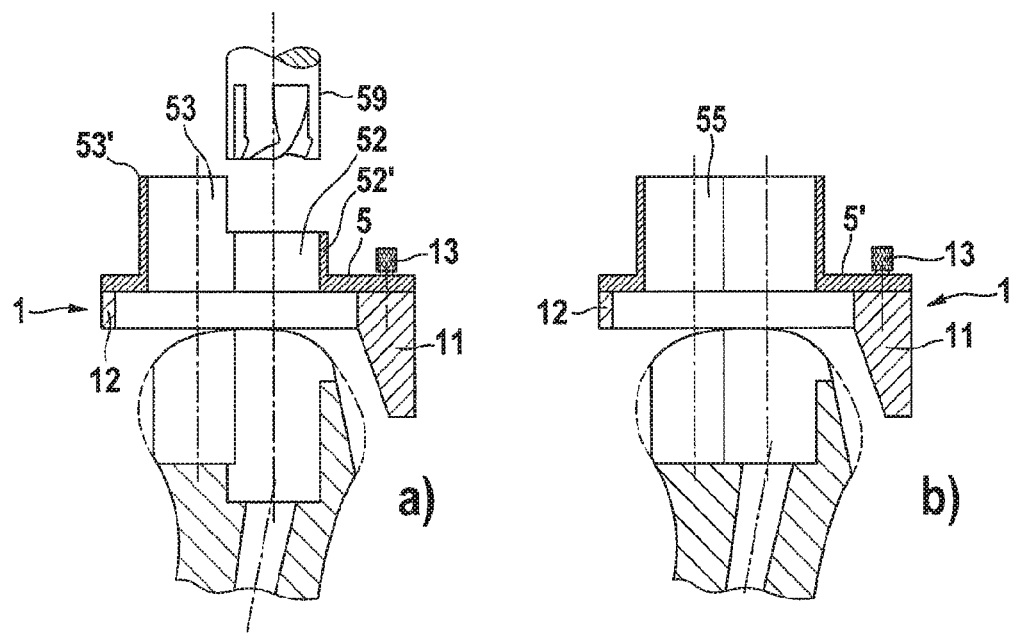
FIG. 22 shows details for use of the second milling gauge according to FIG. 4.
Figure 23:
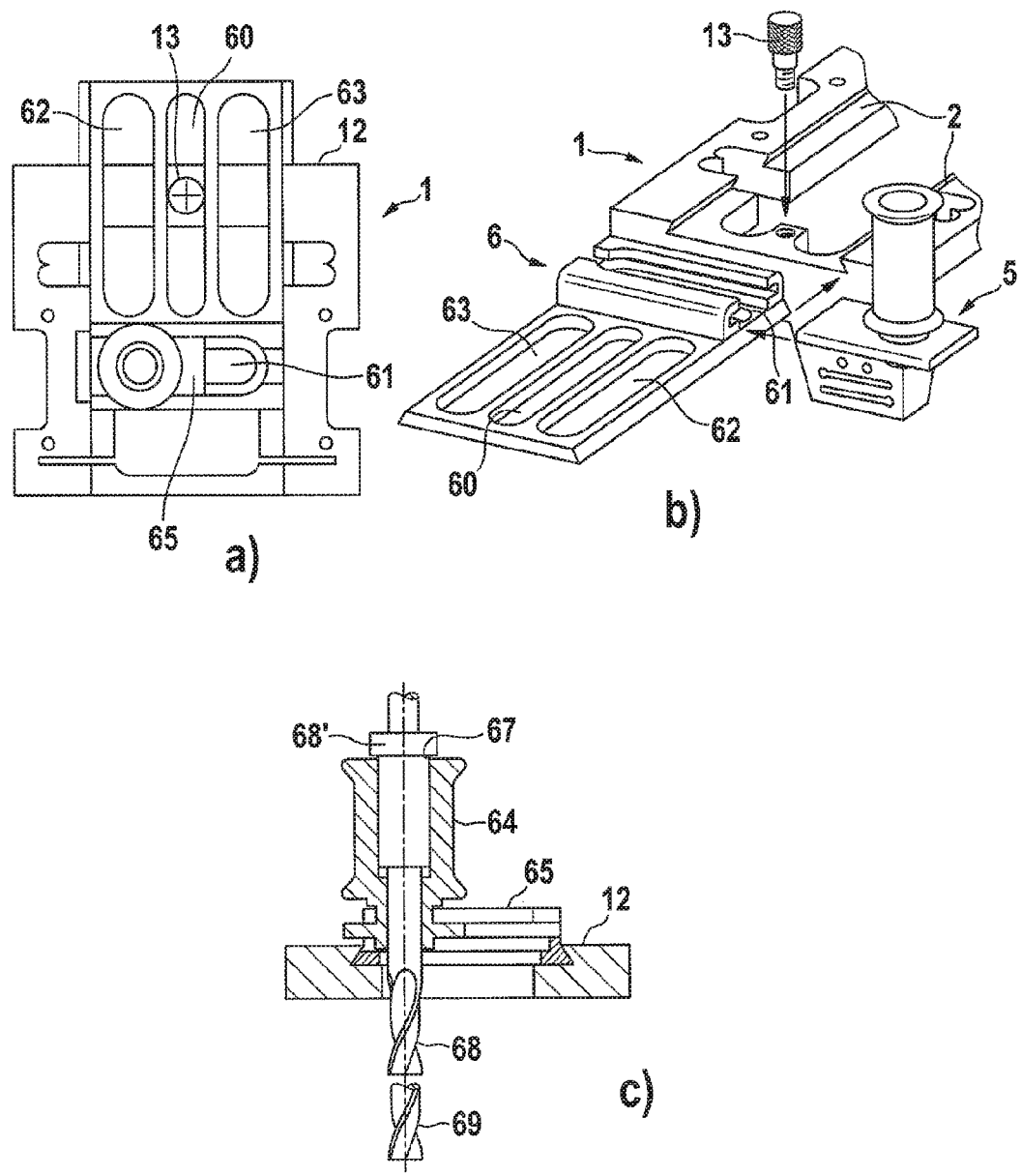
FIG. 23 shows details for use of the slotted link milling gauge according to FIG. 5.

In the following step, the first milling insert 4 is replaced for a second milling insert 5. This has a double receptacle 51, which is octagonal in cross section and forms two receiving positions 52, 53 for a bulk milling cutter 59. The two receptacles 52, 53 are not arranged centrally, but both with a different offset in relation to the side (lateral offset). Each of the two receiving positions 52, 53 is assigned an upwardly protruding sleeve 52', 53'. The bulk milling cutter 59 in its upper region likewise has a protruding collar 59', which cooperates with the upper edge of the sleeve 52', 53' assigned to the respective receptacle 52, 53 and thus forms a depth stop for the bulk milling cutter 59 (see FIG. 22*a*). A large part of the cavity can thus be preformed for the reception of the implant. It is noted that the second milling insert 5, similarly to the first milling insert 4, is positioned clearly on the base frame 1 by means of an opening 54 in line with the central fastening.

Due to the different depth stops of the two receptacles 52, 53 of the double receptacle 51, the cavity in the bone can be efficiently broached. If this is not necessary, a simplified second milling insert 5' can be provided and has a double receptacle 55 without lateral offset. Here, the depth stops may be arranged at the same height however (see FIG. 22*b*); it is not to be ruled out however that they are arranged at different heights (in accordance with the illustration in FIG. 22*a*).

It is further noted that the second milling insert 5 is contained in the set of equipment in two versions. One version is for left-sided implantation, and a second version, which is axially symmetrical, is formed for right-sided implantation (see the milling inserts 5 in FIG. 4 marked by "L" and "R").

In the following step, the second milling insert 5 is replaced by a third milling insert 6, which is formed as a slotted link insert (see FIGS. 5 and 23*a-c*). This has two slotted link windows 60, 61 oriented in a T-shaped manner and two inspection windows 62, 63. The slotted link window 60 is formed as a slot and acts as a receptacle for the fastening screw 13, by means of which the slotted link insert is guided on the base frame 1. The slotted link insert 6 can therefore be moved to and fro frontally and dorsally. A slotted link slider 65 is inserted displaceably into the transversely oriented slotted link window 61 and has a handle 64 with a receptacle 67 for a milling tool 68, 69. The milling tools 68, 69 are a pre-milling cutter and an end-milling cutter, which are designed for different milling depths by means of a stop collar 68', 69' arranged at different distances from the tip (see FIG. 5 and FIG. 23*c*). They can be inserted through a central opening 67 in the handle 64 into the slotted link slider 65. By moving the slotted link slider 65 along its slotted link window 61 and by moving the slotted link insert 6 along the slotted link window 60 (x/y movement), a rectangular cavity cross section can be milled out with high precision. Thanks to the precise slotted link guidance, the cavity can be produced with high dimensional accuracy, and the box-like receiving space for the knee prosthesis can thus be prepared in the femur cavity.

Figure 24:
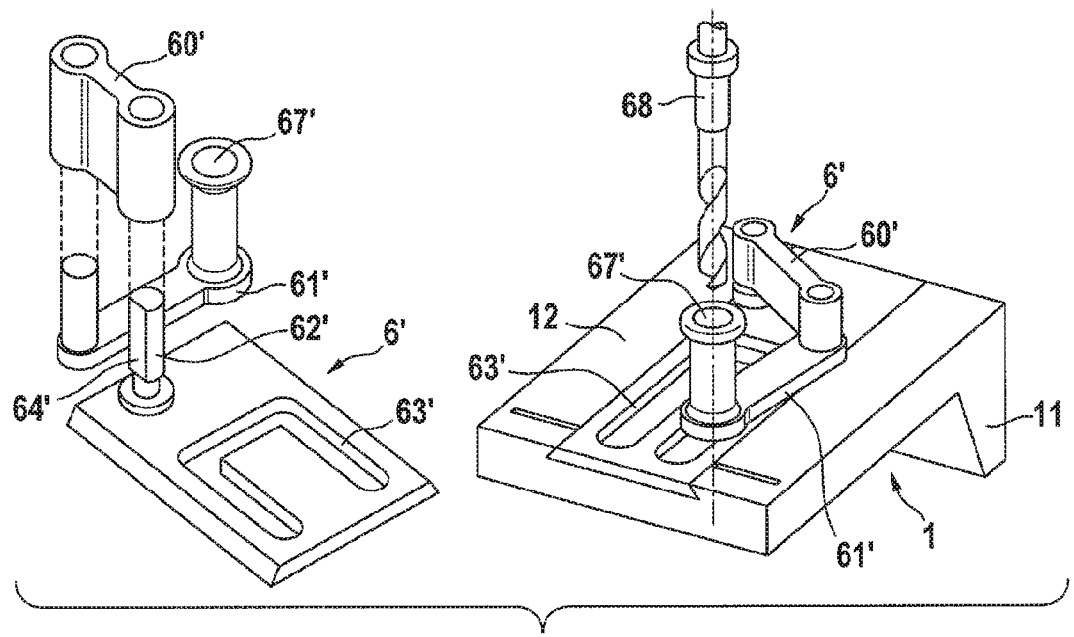
FIG. 24 shows an alternative slotted link milling gauge.

An alternative embodiment for the slotted link insert 6 is illustrated in FIG. 24. It is a hinged slotted link insert 6'. It has two guiding levers 60', 61' hinged to one another. At one end, they are mounted rotatably via a pivot pin 62' on a main plate of the insert 6', and at the other end a receptacle 67' for the milling tools 68, 69 is formed. A U-shaped slotted link path 63' is cut out on the base plate of the slotted link insert 6', and the milling tool 68, 69 inserted into the receptacle 67' is forcibly guided in said path by the guiding levers 60', 61'. The pivot pin 62' is provided with a flattened portion 64', such that the guiding levers 60', 61' can only be fitted thereon and removed therefrom in a predetermined assembly position. The flattened portion 64' is aligned here such that, in the assembly position, the receptacle 67' is arranged aside the slotted link path 63'. It is thus ensured that the assembly and disassembly processes can only be performed when the milling tool 68, 69 is removed.

Figure 25:
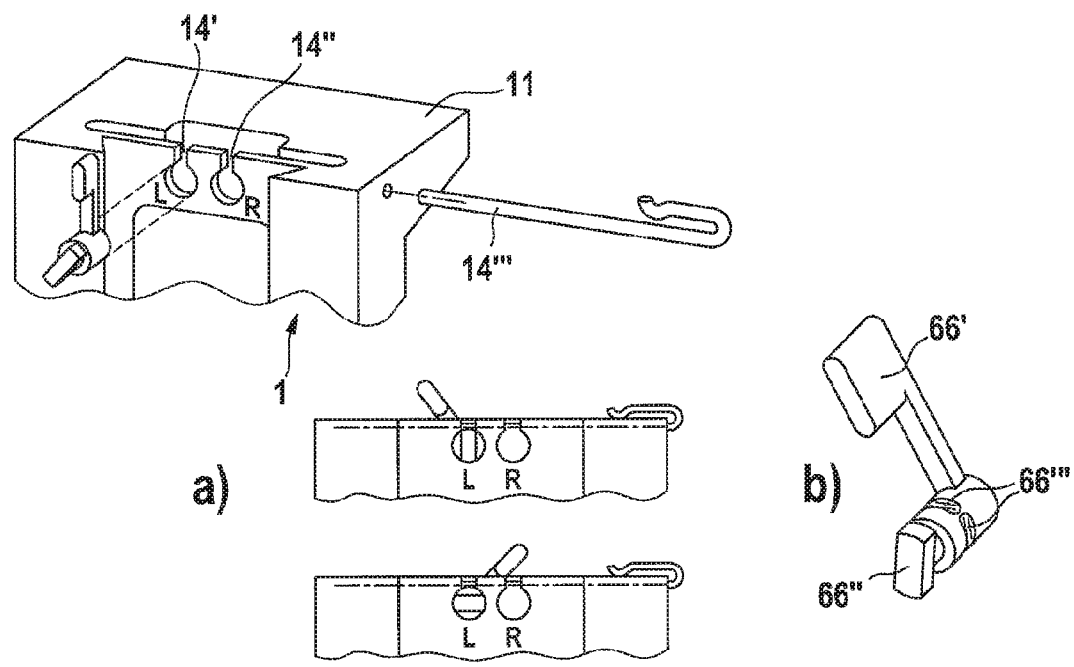
FIG. 25 shows securing devices for inserts.
Figure 26:
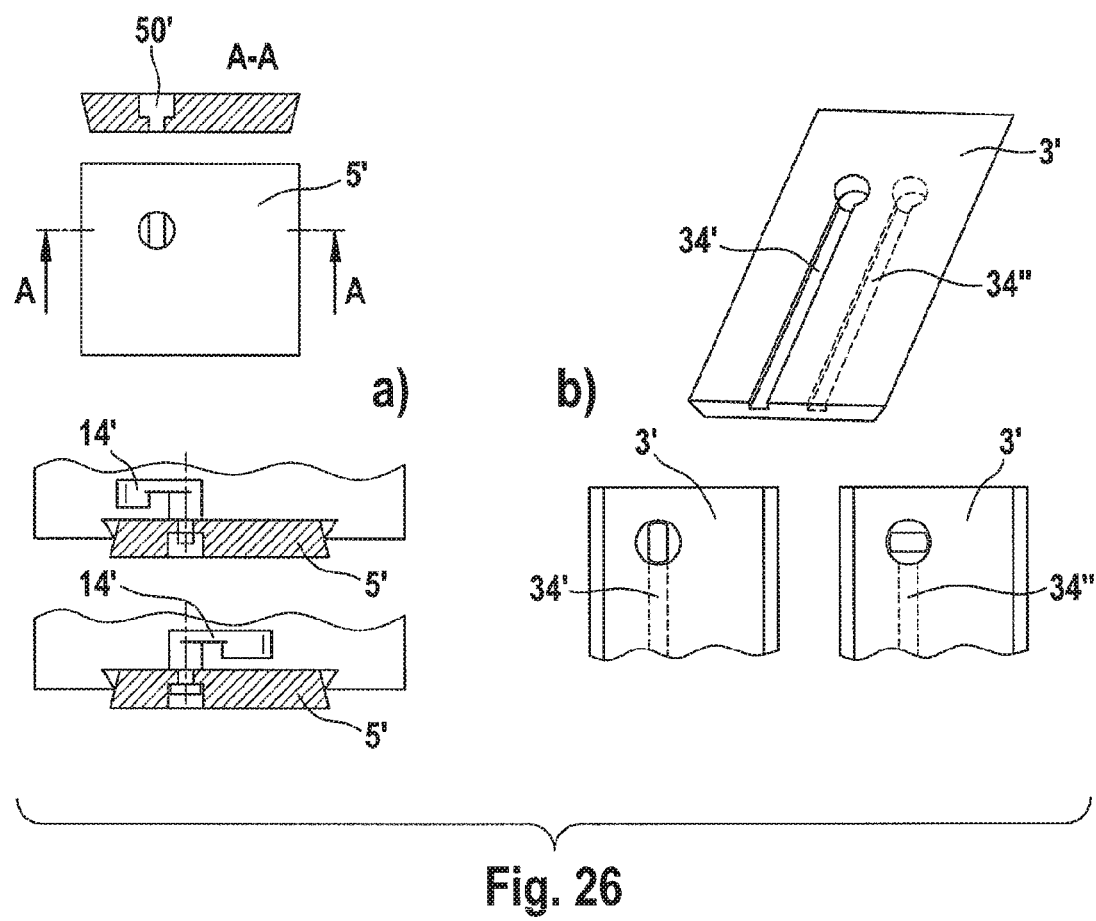
FIG. 26 shows illustrations of the cooperation between securing devices and inserts.

An additional securing of the inserts 3, 4 and 5 in the base frame 1 is illustrated in FIG. 25. The securing opening 14 on the base frame is formed twice, more specifically once for the left-hand side 14' and once for the right-hand side 14". The fastening openings 34, 44 and 54 on the inserts 3, 4 and 5 are formed as grooves 34', 34" running as far as the edge and offset laterally with respect to one another, depending on whether the respective insert is provided for left-side or right-side implantation. A securing lever 66' comprises a toggle 66" at the end of a shaft stump. The securing lever 66' can be inserted in the orientation illustrated in FIG. 25*b* into one of the fastening openings 14', 14" from the side. By moving the securing lever 66', the toggle 66" is moved through a right angle, whereby a locking effect is achieved. In order to avoid accidental actuation of the securing lever 66', a securing bolt 14''' is preferably provided and is inserted into the base frame 1 from the side and rests in an aligned manner against a flattened portion 66''' of the shaft stump, in such a way that the shaft stump and therefore the securing lever 66' are prevented from rotating. The securing lever 66' can then only be moved again when the securing bolt 14''' is removed. The corresponding inserts are expediently provided on their underside with an undercut bore 50' in the case of an insert 5' to be secured against lifting out (see FIG. 26*a*) and/or with the groove 34', 34" and a widened end in the case of an insert 3' to be secured against displacement (see FIG. 26*b*). The open position is illustrated in each of the two smaller images (at the top in FIG. 26*a* and to the left in FIG. 26*b*) as well as the closed position (at the bottom in FIG. 26*a* and to the right in FIG. 26*b*).

Once the box-shaped receiving space has been developed in the femur, the sliding paths on the condyles are then machined. Reference is made in particular to FIGS. 7 to 10. To machine the condyles, the curved milling gauge 7 is used. It is inserted by means of a pair of insertion tongs 75. The pair of tongs comprises two tong halves 78, which, at their front ends, have two grippers 79 cooperating with a form fit with the curved milling cutter 7. On the outer face of the tong halves, aligning lugs 77 pointing away from one another are formed. They are designed such that they are congruent to the shape of the guiding slots 17 on the base frame 1. Precise positioning of the curved milling gauge 7 relative to the base frame 1 is thus ensured by inserting the insertion tongs 75 into the base frame 1, the aligning lugs 77 engaging with a form fit in the guiding slots 17 (see FIG. 10). It is noted that the curved milling gauge 7 is available in different (preferably four) sizes, the positioning by means of the insertion tongs 75 being achieved similarly by form-fitting engagement in the guiding slots 17 irrespective of the size used.

Figure 7:
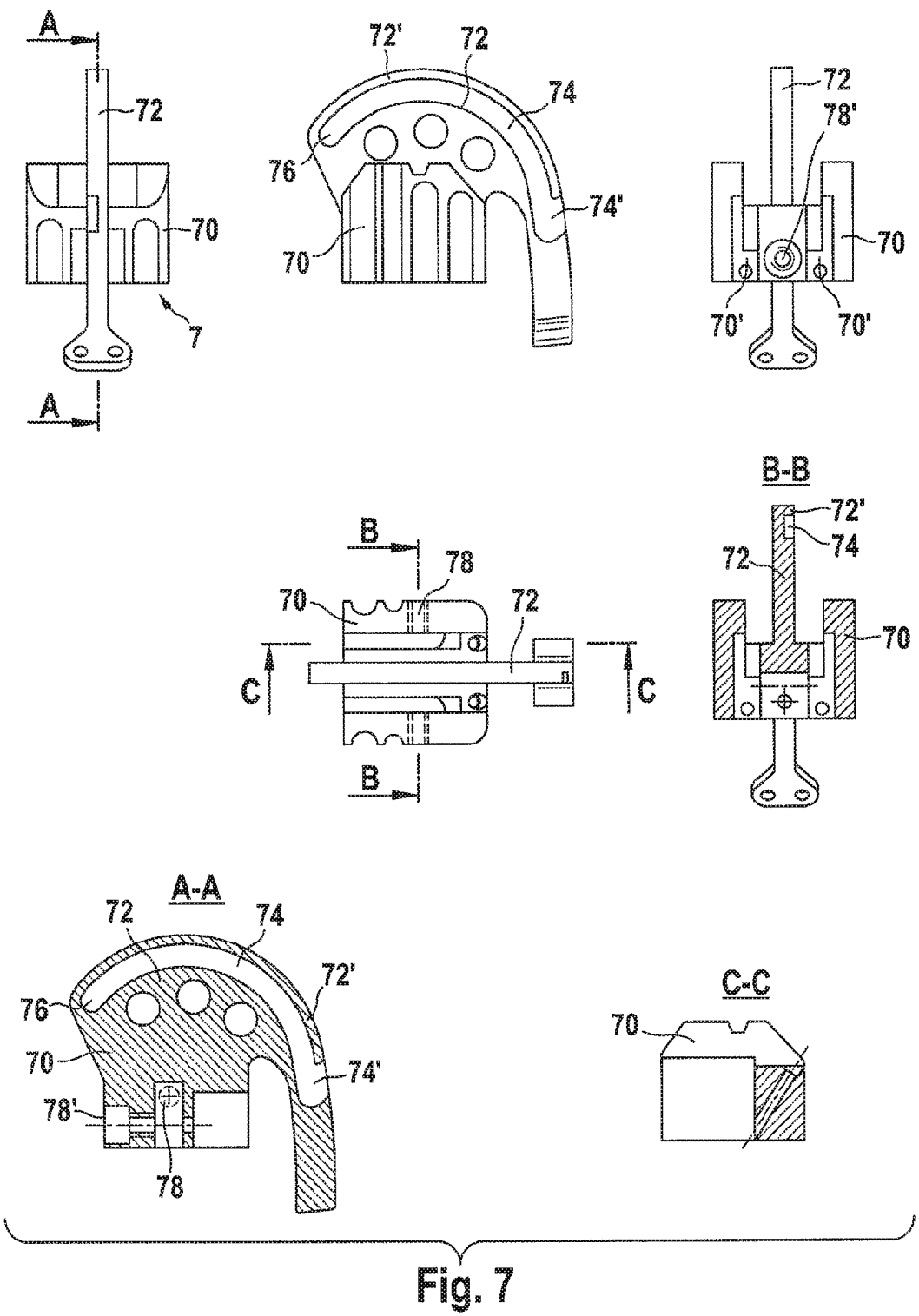
FIG. 7 shows a curved milling gauge comprising a main body.

The curved milling gauge 7 comprises a main body 70, of which the basic shape corresponds approximately to a cuboid-like box (see FIG. 7). Grooves 71 running vertically from top to bottom are formed on the lateral sides of the curved milling gauge. The grooves are used for sturdier and position-maintaining anchoring in the cavity of the femur. On the upper side of the main body 70, an upwardly protruding circular arc segment 72 is formed in one piece and covers an angular range of approximately of 100 to 120 degrees and, in the front region, is pulled down to approximately half the height of the main body 70. In the region close to the edge, it has a recessed guiding path 74 on one of its side faces. Said path is delimited via a web 75 toward the upper edge of the circular arc segment 72, wherein, in the downwardly pointing front region, an extension 74' of the guiding path 74 is formed and is web-free. An opening is thus created, through which a follower 84 of the guiding piece 8 can be inserted into the guiding path 74 or removed therefrom. This can occur only in the position when the follower 84 is located in the region of the extension 74. The guiding path 74 is closed at the other, rear end and forms a stop 76 for the follower 84.

From a rear side of the main body 70, a double slit 77 extends as far as the upper side of the main body 70. A receiving bore for a securing screw 79 is arranged transverse thereto. It acts as a pivot bearing for a toggle linkage 80, of which the free end protrudes from the main body 70 and which is pivotable along the double slit 77 (see FIG. 7). At its free end, the toggle linkage 80 carries a pivot pin 81, of which the cross section is approximately rectangular with straight long sides and circular-arc-shaped convex short sides (see FIG. 11a). Between the circular-arc-shaped convex short sides, the pivot pin 81 has a meridian of greatest width D, and between the straight sides a meridian of smallest width d.

Figure 8:
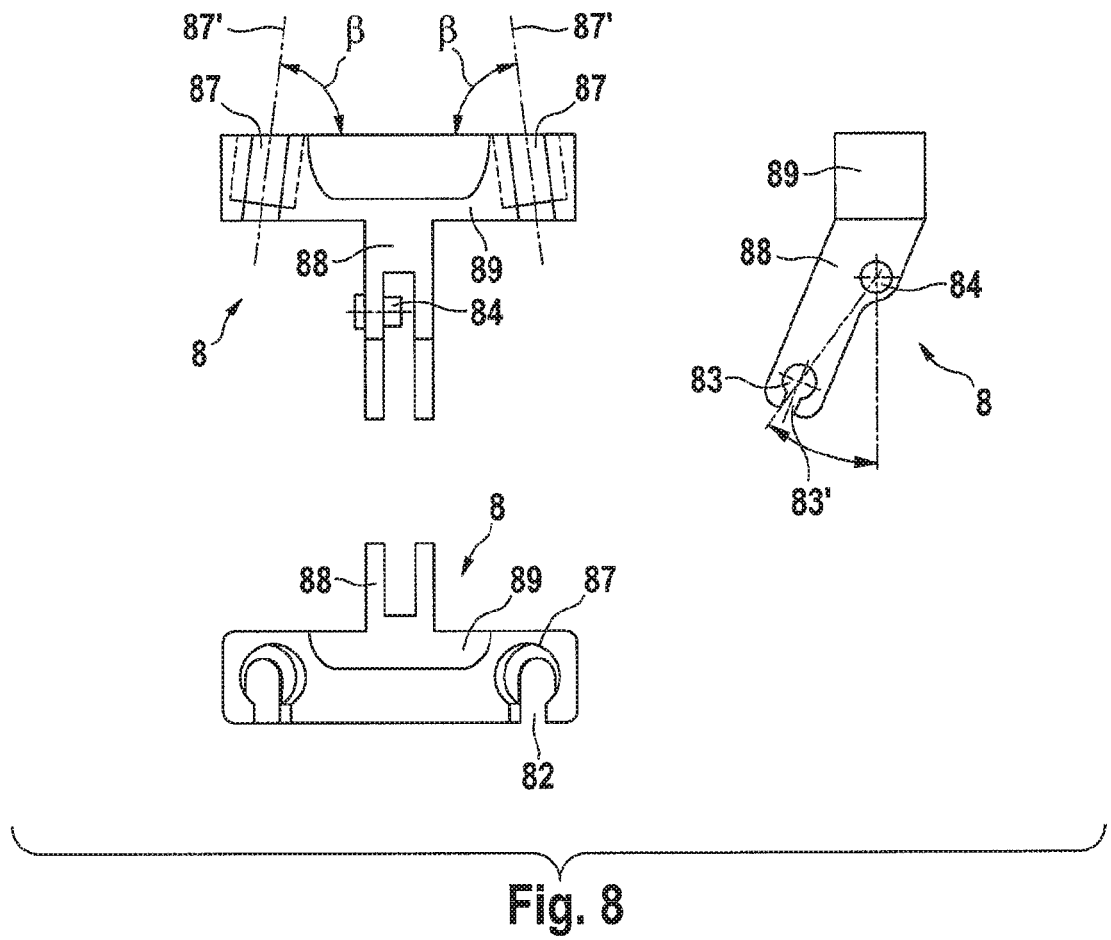
FIG. 8 shows a guiding piece for the curved milling gauge according to FIG. 7.
Figure 9:
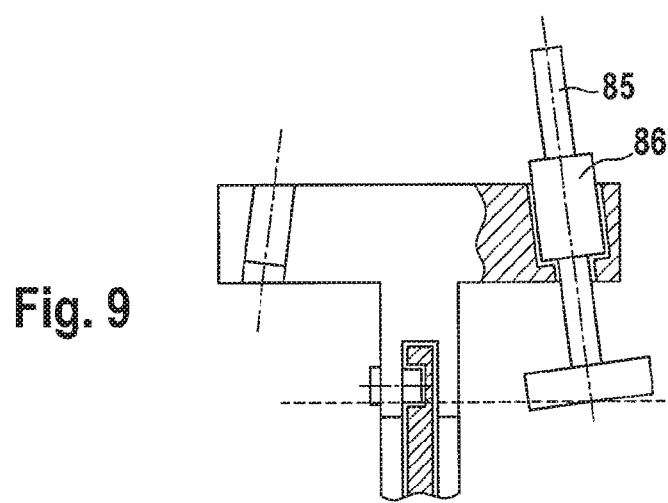
FIG. 9 shows a condyle milling cutter inserted into the guiding piece according to FIG. 8.
Figure 10:
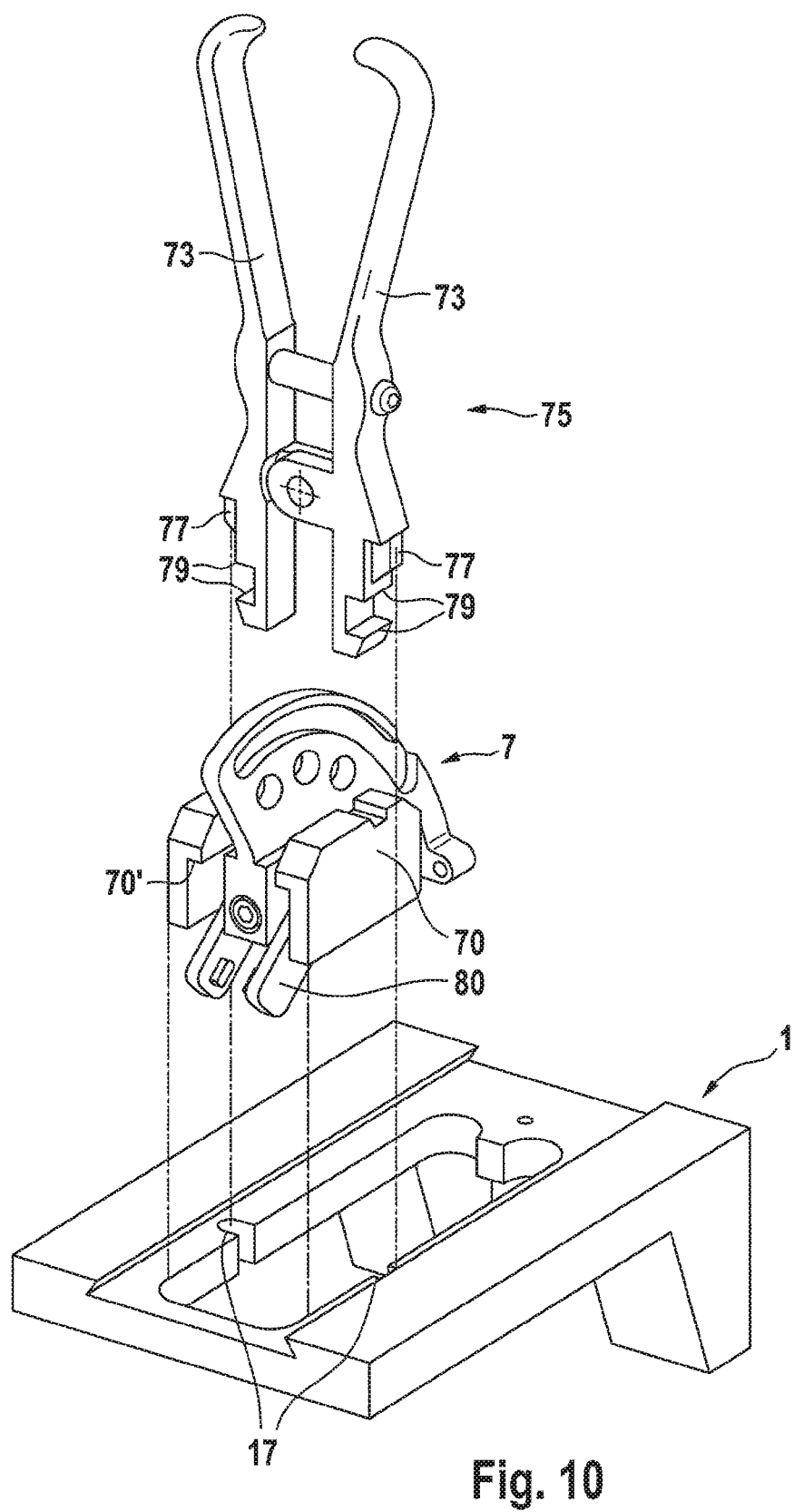
FIG. 10 shows a pair of insertion tongs for inserting the curved milling gauge into the base plate.
Figure 11:
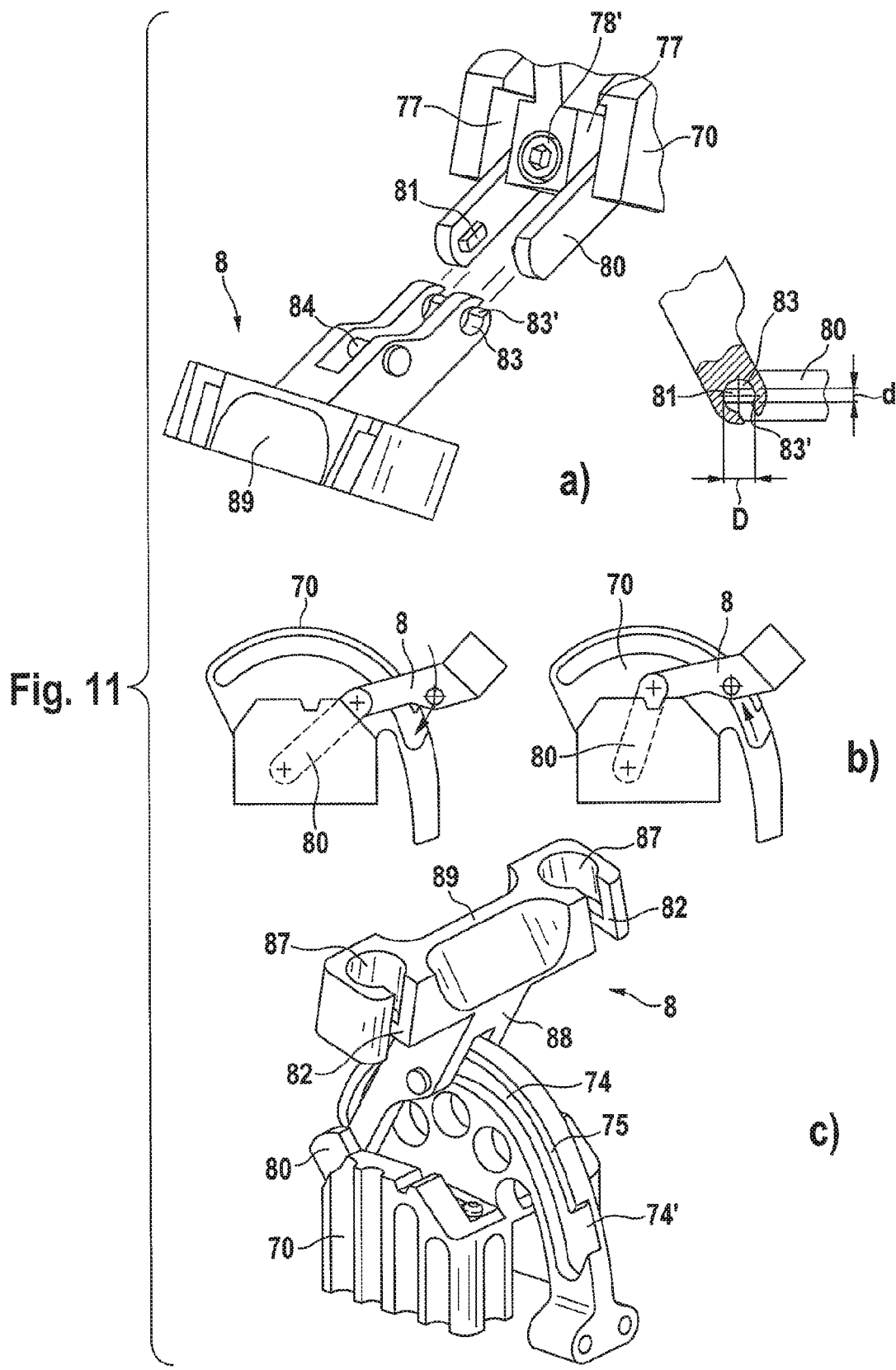
FIG. 11 shows individual illustrations for arranging the guiding piece on the main body of the curved milling gauge.

The guiding piece 8 is generally of T-shaped design with a transverse segment 89 and a longitudinal segment 88 (see FIG. 8). In each of the outer regions, a stepped bore 87 with a peripheral shoulder is arranged on the transverse segment 89. Said stepped bores are oriented with their axis 87' such that they form an angle α from 75 to 85 degrees, preferably 80 degrees, to the transverse segment 89. The axes 87' are therefore divergent. The stepped bore 87 forms a guide for a condyle milling cutter 85, which is inserted via a lateral opening 82 into the stepped bore 87. The condyle milling cutter 85 comprises a milling head and a shaft, on which a cylindrical thickening 86 distanced from the milling head is formed. Since it is placed on the peripheral shoulder of the stepped bore 87, it delimits the milling depth.

The longitudinal segment 88 of the guiding piece 8 is angled; it forms an angle from approximately 15 to 25 degrees, preferably 20 degrees, to the plane spanned by the axes 87'. The follower 84 is arranged laterally on the longitudinal segment 88 and guides the guiding piece 8 along the guiding path 74. At the free end, the longitudinal segment 88 is formed in a fork-like manner and is provided with a transverse bore, which acts as a pivot bearing sleeve 83. It is open toward the free end via a constriction 83'. The width of the constriction 83' is dimensioned such that it is larger than the meridian of smallest width 82 and smaller than the meridian of greatest width 82'. If the pivot bearing sleeve 83 and the pivot pin 81 are oriented such that the constriction 83' contacts the meridian of smallest breadth 82, the guiding piece 8 can be pushed with its pivot bearing sleeve 83 onto the pivot pin 81, and in any other orientation the pivot pin 81 is prevented from passing through the constriction 83'. An angular lock is thus provided, which can be opened and closed only in one position and is otherwise locked (see FIGS. 11a and b).

The pivot pin 81 is oriented on the toggle linkage 80 such that the guiding piece 8 can be coupled and removed only in an elongate position when the guiding piece 8 forms a line with the toggle linkage 80 (see FIG. 11a).

If the guiding piece 8 is coupled, it is inserted via its follower 84 in the region of the extension 74' into the guiding path, the guiding piece 8 being arranged at an angled position (that is to say no longer elongate) relative to the toggle linkage 80. The pivot pin 81 is therefore prevented from passing through the constriction 83'. The guiding piece 8 inserted into the guiding path 74 is therefore locked securely to the toggle linkage 80 (see FIG. 11b).

The kinematics thus achieved for the guidance of the condyle milling cutter 85 is illustrated in FIG. 12 as a multi-phase diagram. The pivot bearing 78 is illustrated at the bottom in the middle of the image. It forms a fixed pivot point for the curve guidance consisting of guiding path 74, guiding piece 8, and toggle linkage 80. The guiding piece 8 is guided via its follower 84 over the entire pivot range along the guiding path 74. The guiding path 74 has an increasing curvature (from left to right in the figure), whereby the radial distance between the pivot bearing 78 and follower 84 increases. As a result, not only does the condyle milling cutter 85 inserted into the guiding piece 8 become increasingly removed from the pivot bearing 78 (it thus describes an arc becoming continuously greater), but it also changes its orientation. Due to the articulation via the toggle linkage 80, the guiding piece rotates, such that the axis 87 for the milling cutter 85 is directed toward the pivot bearing 78 at the start of the pivot motion, but rotates increasingly dorsally (to the right in FIG. 12) with the movement of the guiding piece 8 along the guiding path. A condyle shape is thus produced on the bone by means of the milling cutter 85, the current center of rotation of the milling cutter not being stationary as the knee joint flexes, but shifting dorsally. A path of movement that corresponds practically fully to that of the natural knee and is therefore physiologically extremely favorable is thus enabled for the knee prosthesis implanted using the equipment according to the invention. Knee prostheses implanted in this way provide the best preconditions for long-term therapy success without the need for revision surgery after a short period of time.

An alternative embodiment of the guiding piece for different condyle milling is illustrated in FIGS. 13a and b. In this case, guiding pieces 8', 8'' are provided and receive a horizontal milling cutter 85', 85''. In the variant illustrated in FIG. 13a, the horizontal milling cutter 85' is mounted from the side into the guiding piece 8', and is mounted there in a one-sided manner. The movement kinematics corresponds to that illustrated in FIG. 12. In the variant illustrated in FIG. 13b, the toggle linkage and the guiding piece 8'' are arranged externally, and the horizontal milling cutter 85'' is inserted through the guiding piece 8''. In this variant, it is necessary to reassemble the toggle linkage and the guiding piece 8'' in order to machine the other side.

The equipment further comprises an awl set for creating and preparing a prosthesis receptacle in the femur. The awl set (see FIG. 6) comprises an access awl 90, which is used to open the medullary cavity of the femur. By means of reamers 91, which are preferably contained in the set in different lengths and diameters, the medullary cavity is enlarged successively. The special rasp/broaching awl 92 with the stop plate 97 is further provided and has already been described above. Lastly, a pin-hole drill 98 with stop is provided and is inserted into the drill guides 18 in order to form receptacles for anchoring pins (not illustrated) on a condyle part of the knee joint endoprosthesis.

The invention claimed is:

1. A set of equipment for inserting a joint prosthesis, at the end of a bone, comprising
   a base frame comprising a guiding plate and a primary gauge protruding laterally from the guiding plate,
   a fastening device for arranging the base frame on the bone in a fixed position,
   a curved milling gauge with a main body and a guiding piece, the guiding piece being movable along a curved guide of the main body and comprising a receptacle for an abrasive tool, and an aligning feature for positioning the curved milling gauge in a predefined position relative to the base frame when the curved milling gauge is inserted into the base frame.

2. The equipment of claim 1, wherein the curved guide has a non-constant curvature.

3. The set of equipment of claim 2, wherein the curved guide has continuously varying curvature.

4. The set of equipment of claim 2, wherein the respective center of curvature moves over a path from 2 to at most 6 mm.

5. The set of equipment of claim 1, wherein the guiding piece is mounted via a follower to the curved guide and via a pivot bearing pivotably to the main body.

6. The set of equipment of claim 5, wherein the pivot bearing is arranged at a distance from the follower and has a toggle linkage mounted pivotably on either side of the pivot bearing.

7. The set of equipment of claim 6, wherein the toggle linkage is mounted removably on the main body.

8. The set of equipment of claim 5, wherein the guiding piece is removable.

9. The set of equipment of claim 8, comprising an angular lock between the guiding piece and the main body that can be separated by moving the guiding piece into an extension of the curved guide.

10. The set of equipment of claim 9, wherein the angular lock comprises a pivot bearing sleeve and a non-circular pivot pin that is disengagable from the pivot bearing sleeve in only one angular position of the guiding piece.

11. The set of equipment of claim 10, wherein the pivot bearing sleeve is open at one side via a constriction, the pivot pin having a meridian of smallest width and a meridian of greatest width, and the breadth of the constriction is sufficient for the passage of the meridian of smallest width but not of greatest width.

12. The set of equipment of claim 5, wherein the receptacle comprises a longitudinal axis that is arranged at an oblique angle to a line connecting a center point of the follower and a center point of the pivot bearing.

13. The set of equipment of claim 12, wherein the angle lies in the range between 10 and 35 degrees.

14. The set of equipment of claim 12, wherein the angle lies is the range between 15 and 30 degrees.

15. The set of equipment of claim 12, wherein the receptacle for the abrasive tool on the guiding piece cooperates with a depth stop.

16. The set of equipment of claim 15, wherein the depth stop is formed by a stepped seat in the receptacle.

17. The set of equipment of claim 16, wherein a side of the stepped seat includes an opening.

18. The set of equipment of claim 12, wherein the guiding piece has two receptacles for the abrasive tool.

19. The set of equipment of claim 18, wherein the double receptacle has divergent axes such that the abrasive tool points outwardly in the inserted state.

20. The set of equipment of claim 5, wherein the guiding piece with the pivot bearing can be disassembled from one side of the main body and reassembled on the other side of the main body.

21. The set of equipment of claim 1, wherein fastening bores are provided on one or both of the main body and the curved guide.

22. The set of equipment of claim 1, wherein an aligning insert is removably arranged on the guiding plate in a predefined position and is configured to receive an aligning body.

23. The set of equipment of claim 22, wherein the aligning body comprises a bone broaching tool.

24. The set of equipment of claim 22, wherein the guiding plate comprises a receptacle for the aligning body and the receptacle for the aligning body comprises an opening on one side.

25. The set of equipment of claim 1, comprising a frontal-sawing insert having two kerfs aligned in a V-shaped manner relative to one another and being configured fasten to the base frame in two positions.

26. The set of equipment of claim 1, comprising spacers of different thicknesses and the spacers are configured for arrangement on either side on the edge of the guiding plate.

27. The set of equipment of claim 1, wherein a first milling insert can be removably attached to the guiding plate and forms a defined receptacle for a broach milling cutter.

28. The set of equipment of claim 27, wherein the receptacle holds the milling cutter in a position and forms a depth stop.

29. The set of equipment of claim 1, comprising a feeler gauge that can be plugged into a plug receptacle on the guiding plate in an angled manner with respect to the guiding plate.

30. The set of equipment of claim 1, wherein a second milling insert can be removably attached to the guiding plate and comprises two receptacles for receiving a bulk milling cutter so that the cutter can be plugged into either of the two receptacles.

31. The set of equipment of claim 30, wherein the two receptacles have different depth stops and lateral offsets.

32. The set of equipment of claim 1, wherein a second auxiliary milling insert can be removably attached to the guiding plate and comprises two receptacles for receiving a bulk milling cutter so that the cutter can be plugged into either of the two receptacles.

33. The set of equipment of claim 32, wherein the double receptacle has one or both of identical depth stops and no lateral offset.

34. The set of equipment of claim 1, wherein a third milling insert can be attached to the guiding plate and comprises a slotted link guide for a depth milling cutter.

35. The set of equipment of claim 34, wherein the depth milling cutter is received in a slotted link slider that is configured to slide relative to the slotted link guide.

36. The set of equipment of claim 35, wherein the slotted link slider has a handle.

37. The set of equipment of claim 36, wherein the slotted link slider comprises a depth stop for interfacing with a collar of the depth milling cutter.

38. The set of equipment of claim 35, wherein the slotted link guide comprises a slotted link window in which the slotted link slider can be received.

39. The set of equipment of claim 34, wherein the slotted link guide comprises two guiding levers connected to one another in a hinged manner, the receptacle for the depth milling cutter is arranged at one end of the connected guiding levers, and another end of the connected guiding levers is pivotably attached to an insert on the guiding plate.

40. The set of equipment of claim 1, wherein the guiding plate has a linear slot for different inserts.

41. The set of equipment of claim 40, wherein the linear slot is a dovetail guide.

42. The set of equipment of claim 1, comprising curved milling gauges in different sizes.

43. The set of equipment of claim 1, comprising a pair of insertion tongs for the curved milling gauge that engages in a form-fitting manner in a predefined position on the curved milling gauge and cooperates via aligning lugs with the aligning feature such that the curved milling gauge is inserted in a predefined position relative to the guiding plate.

44. The set of equipment of claim 1, comprising aligning rods that can be arranged on sides of the base frame pointing away from one another.

45. The set of equipment of claim 1, comprising a drill with depth stop for creating receptacles of anchoring pins of the joint prosthesis.

46. The set of equipment of claim 1, comprising different awls for reaming a concavity on the bone.

47. The set of equipment of claim 46, wherein the concavity comprises a medullary cavity in the femur.

48. The set of equipment of claim 1, comprising a rasp/broaching awl that comprises a shaft that has a recess with a reduced thickness that is configured to receive a stop plate.

49. The set of equipment of claim 48, wherein the rasp/broaching awl has two, three or four cutting edges.

50. The set of equipment of claim 49, wherein the cutting edges comprise teeth that are configured so that teeth of a first cutting edge are vertically offset relative to teeth of a second cutting edge.

51. The set of equipment of claim 1, comprising an aligning gauge for positioning the base frame via the aligning feature.

52. The set of equipment of claim 1, wherein the joint prosthesis comprises a femur component of a knee prosthesis and the bone is a femur.

* * * * *